(12) United States Patent
Meyer et al.

(10) Patent No.: US 8,017,094 B2
(45) Date of Patent: Sep. 13, 2011

(54) RACK FOR ANALYZER AND ANALYZER COMPRISING SUCH A RACK

(75) Inventors: Thomas Meyer, Cham (CH); Reto Schorno, Adligenswil (CH); Thomas Schlaubitz, Meggen (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 1081 days.

(21) Appl. No.: 11/250,903

(22) Filed: Oct. 14, 2005

(65) Prior Publication Data
US 2006/0093529 A1 May 4, 2006

(30) Foreign Application Priority Data
Nov. 4, 2004 (EP) .................................... 04078041

(51) Int. Cl.
*B01L 9/06* (2006.01)
(52) U.S. Cl. ........ 422/560; 422/561; 422/562; 366/110; 366/111; 366/112; 366/208; 366/237; 366/239; 366/240; 366/219
(58) Field of Classification Search .................. 422/104, 422/560–562; 366/110–112, 208–219, 237, 366/239, 240
See application file for complete search history.

(56) References Cited

U.S. PATENT DOCUMENTS

| 5,632,388 A | 5/1997 | Morrison et al. ................ 211/74 |
| 5,665,309 A | 9/1997 | Champselx et al. ............ 422/63 |
| 2003/0044323 A1* | 3/2003 | Diamond et al. ............ 422/102 |

FOREIGN PATENT DOCUMENTS
WO  WO 98/57739   12/1998
WO  WO 01/28680 A3   4/2001

OTHER PUBLICATIONS
EP Serach Report 04078041.3, May 4, 2005.
* cited by examiner

*Primary Examiner* — Brian Gordon
*Assistant Examiner* — Shogo Sasaki
(74) *Attorney, Agent, or Firm* — Reza Savari; Olga Kay; Vivien Banholzer

(57) ABSTRACT

A rack for holding containers containing liquids used in clinical chemistry analyzers. The rack comprises
  (a) a frame having two or more sections, each section being adapted for receiving a liquid containing component,
  at least one of the sections of the frame being adapted for receiving a first liquid containing component which is adapted for being removably but tightly mechanically connected to said frame,
  (b) at least one movable part adapted to be removably coupled to a shaker device, the movable part being adapted for receiving and holding a second liquid containing component,
  at least one of the sections of the frame being adapted for receiving the movable part and allowing motion of the movable part within predetermined limits.

4 Claims, 23 Drawing Sheets

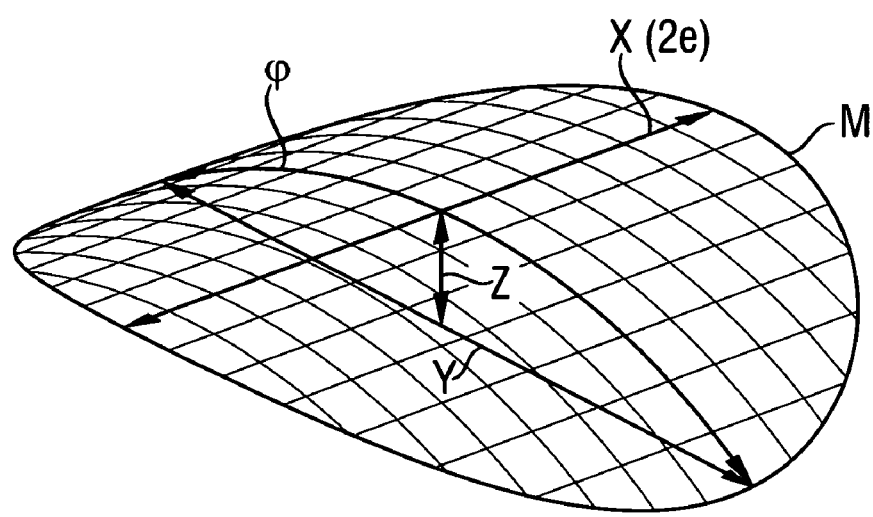
Fig. 8
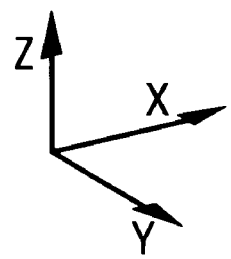

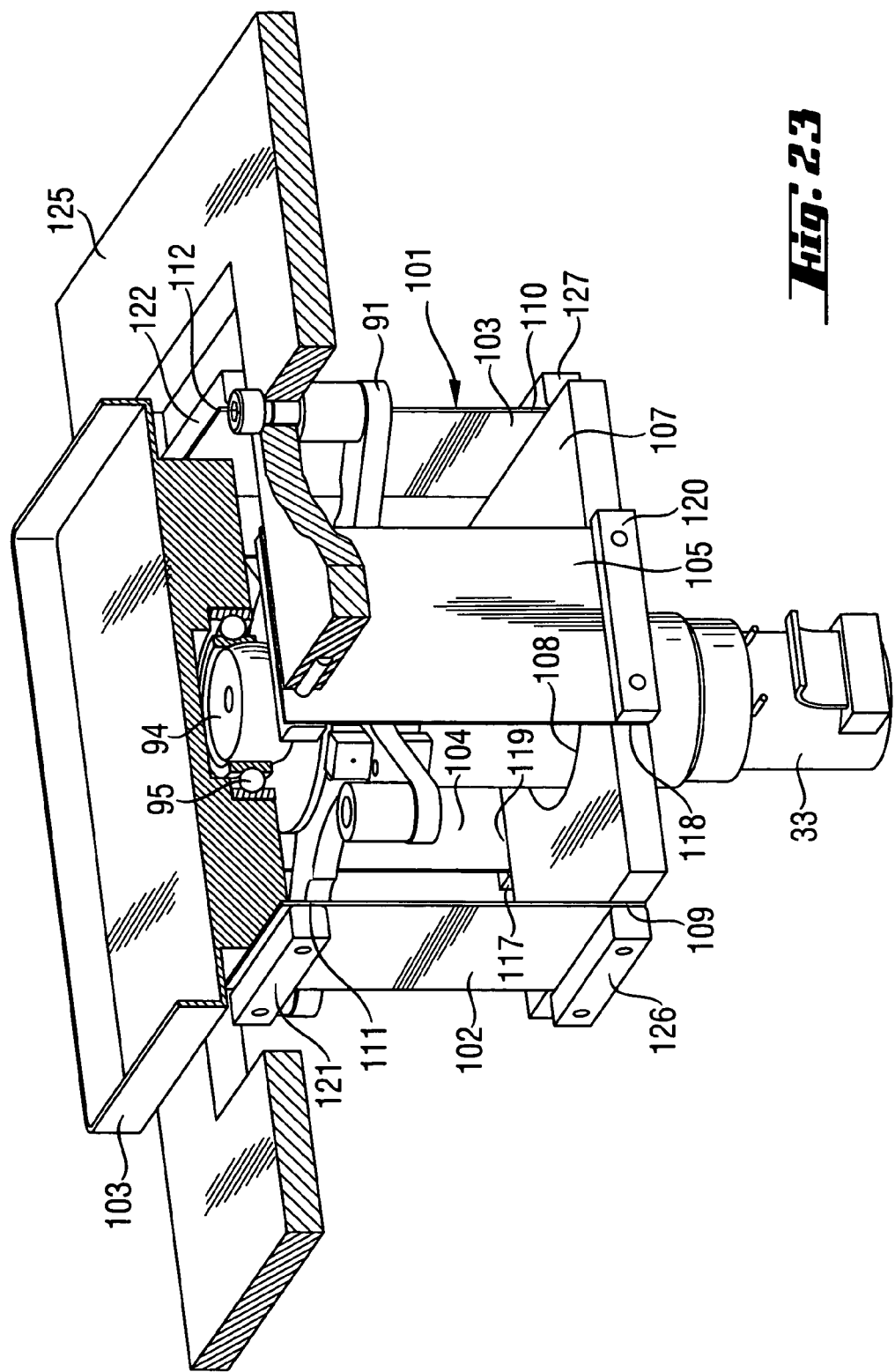

US 8,017,094 B2

RACK FOR ANALYZER AND ANALYZER COMPRISING SUCH A RACK

BACKGROUND OF THE INVENTION

This application claims the benefit of priority under 35 U.S.C. §119 of EP Application 04078041.3, filed Nov. 4, 2004, the contents of which are hereby incorporated by reference.

FIELD OF THE INVENTION

The invention concerns a rack for holding containers containing liquids.

The invention further concerns an automatic analyzer for analyzing biological samples.

DESCRIPTION OF RELATED ART

In automatic clinical chemistry analyzers racks are used for holding containers of liquids required for performing analysis of samples to be analyzed. Some of those liquids are e.g. solutions containing magnetic particles which should be uniformly distributed in the solution; such liquids require agitation during predetermined time intervals, whereas other required liquids require no agitation at all.

In prior art apparatuses it has therefore been necessary to have additional racks for containers which contain liquids that require agitation and agitating means connectable to such racks or to selectively transport such containers to a station for agitating liquid containers and thereby the liquids contained therein. A disadvantage of both approaches is that they increase the complexity and the manufacturing cost of automatic clinical chemistry analyzers. It is therefore desirable to have racks and analyzers which do not have this disadvantage.

SUMMARY OF INVENTION

According to the intended use of the rack defined by claim 1, a container containing a liquid which has to be agitated is placed on a movable part of the rack which is adapted to be shaken by means of a shaker mechanism.

There is also a need for an analyzer having a low cost shaker device which is suitable for agitating liquids e.g. reagents contained in reagent containers located in a rack used in automatic clinical chemistry analyzers. An example of such liquid reagents are those containing magnetic particles which should be agitated in order that the magnetic particles are homogeneously distributed in the liquid.

The subject invention will now be described in terms of its preferred embodiments with reference to the accompanying drawings. These embodiments are set forth to aid the understanding of the invention, but are not to be construed as limiting.

BRIEF DESCRIPTION OF THE FIGURES

FIG. 8 shows a path M of a point of casing 16 when it is moved by shaker device 31 of FIG. 4.

FIG. 23 shows a variant of the embodiment of FIG. 22.

DETAILED DESCRIPTION OF THE INVENTION

An automatic clinical chemistry analyzer comprises in general means for handling liquids like biological samples or reagents and means for analyzing sample-reagent-mixtures. A reagent can be e.g. a liquid containing magnetic particles.

In the following description only those parts of an automatic clinical chemistry analyzer are described which are necessary to describe how a rack containing liquid containers or a movable part of such a rack is agitated by means of a shaker device.

EXAMPLES

Example 1

Example of a Rack According to the Invention

Figure 1:
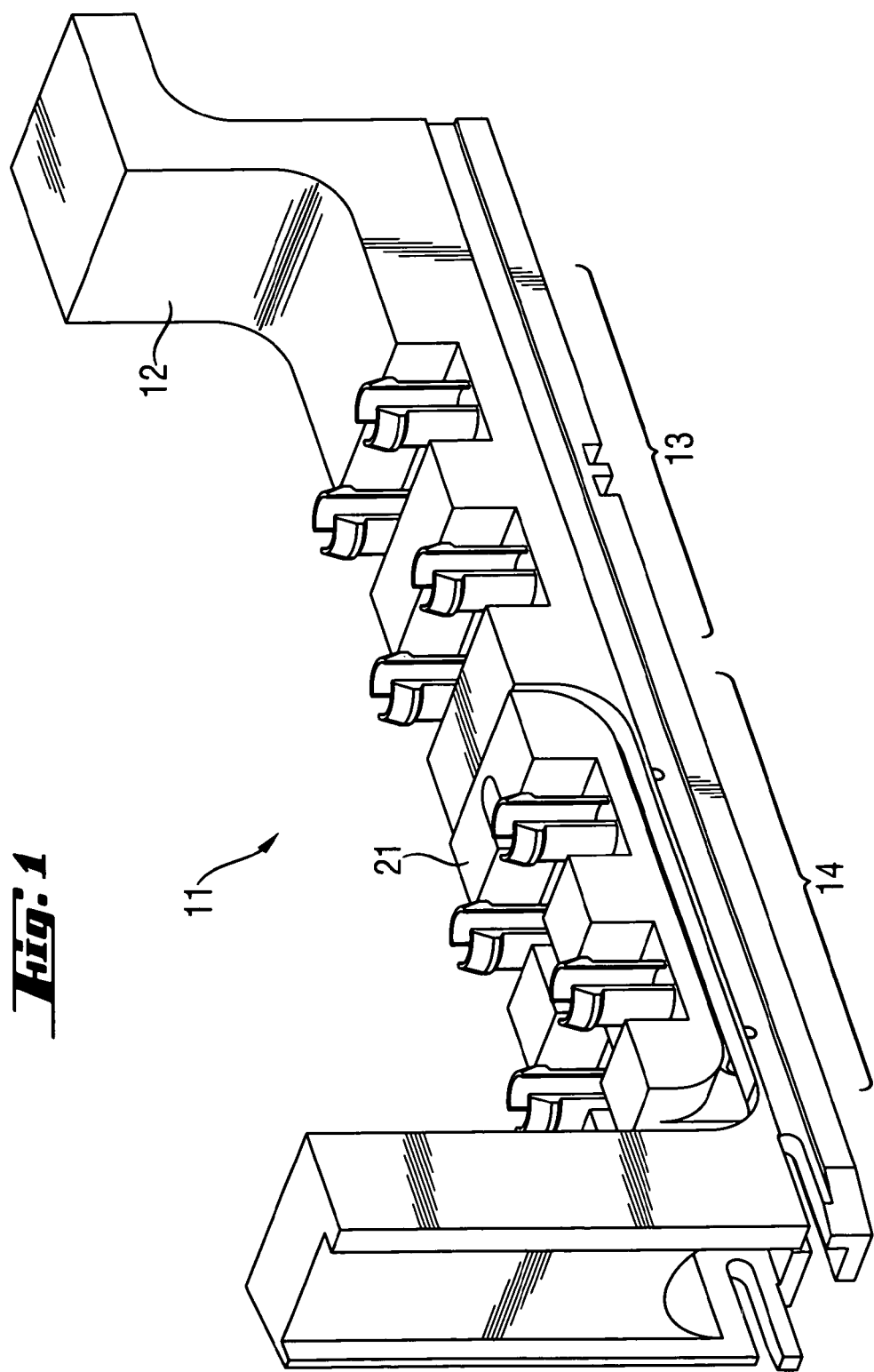
FIG. 1 shows a perspective view of a rack according to the invention.

FIG. 1 shows a rack 11 according to the invention. Rack 11 has a frame 12 and a movable part 21. Frame 12 has at least one section 13 for holding a first liquid containing component (not shown) which does not have to be agitated and at least one section 14 for holding a second liquid containing component (not shown) which has to be agitated. The movable part 21 of the rack 11 is located in a section 14. The shape and size of section 14 allows movement of movable part 21 within predetermined limits.

Rack 11 may be made of any suitable material, such as, for instance a polycarbonate (PC).

Figure 2:
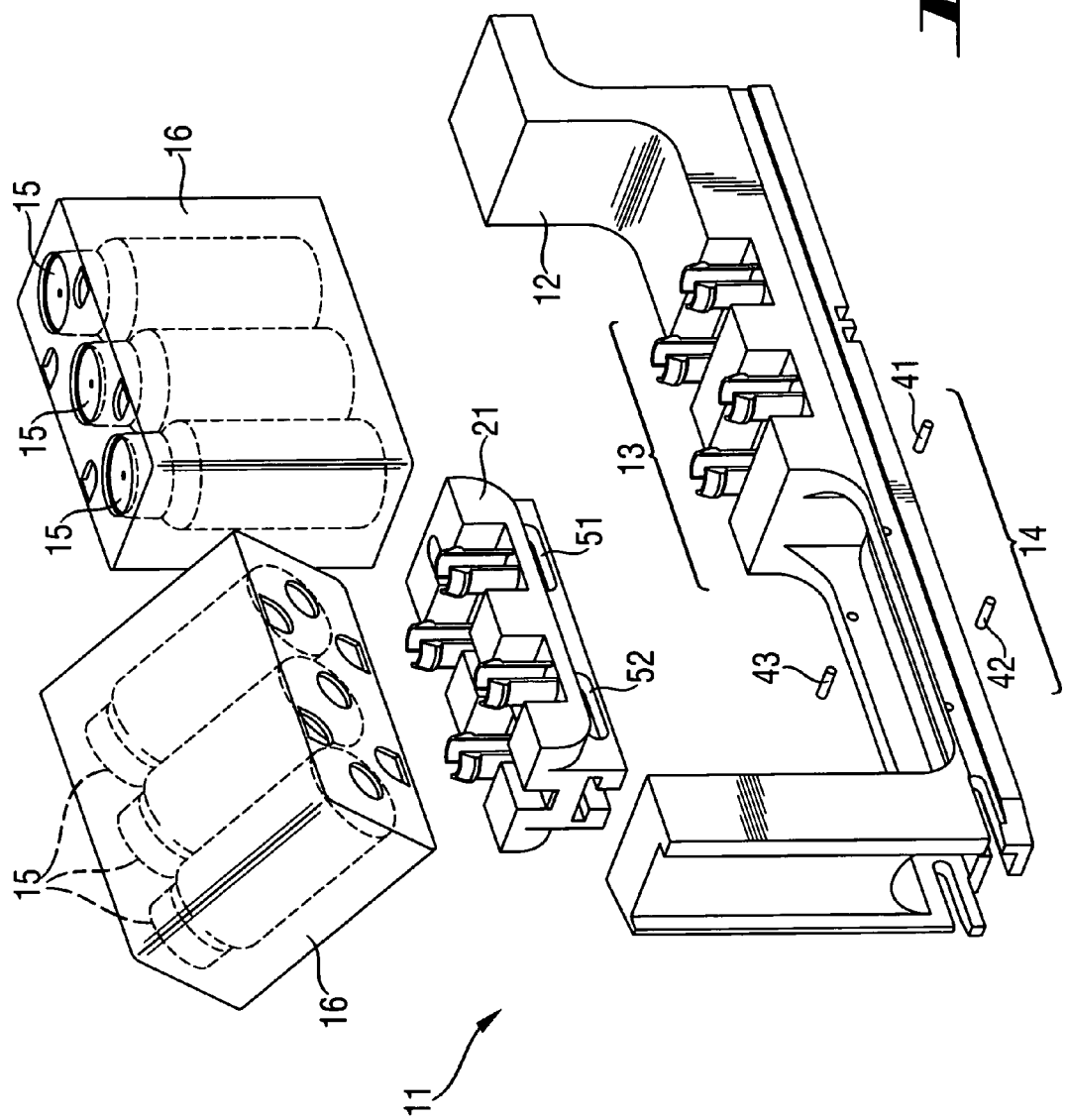
FIG. 2 shows an exploded view of the rack of FIG. 1, removable part 21 of rack 11 and a casing 16 containing several containers 15 which each contain a liquid to be agitated.

The first and the second liquid containing components may be a single liquid container or a component comprising a casing 16 which contains one or more liquid containers 15 (see FIG. 2). A component of the latter type is described in European Patent Application EP 0564970 A2.

FIG. 2 shows a rack 11 having a section 14 that holds a liquid containing a component of the type described in European Patent Application EP 0564970 A2. Such a component comprises e.g. a casing 16 wherein one or more containers 15 are lodged. Each of the containers 15 contains a liquid to be agitated.

Example 2

Example of a First Embodiment of an Analyzer According to the Invention

Figure 3:
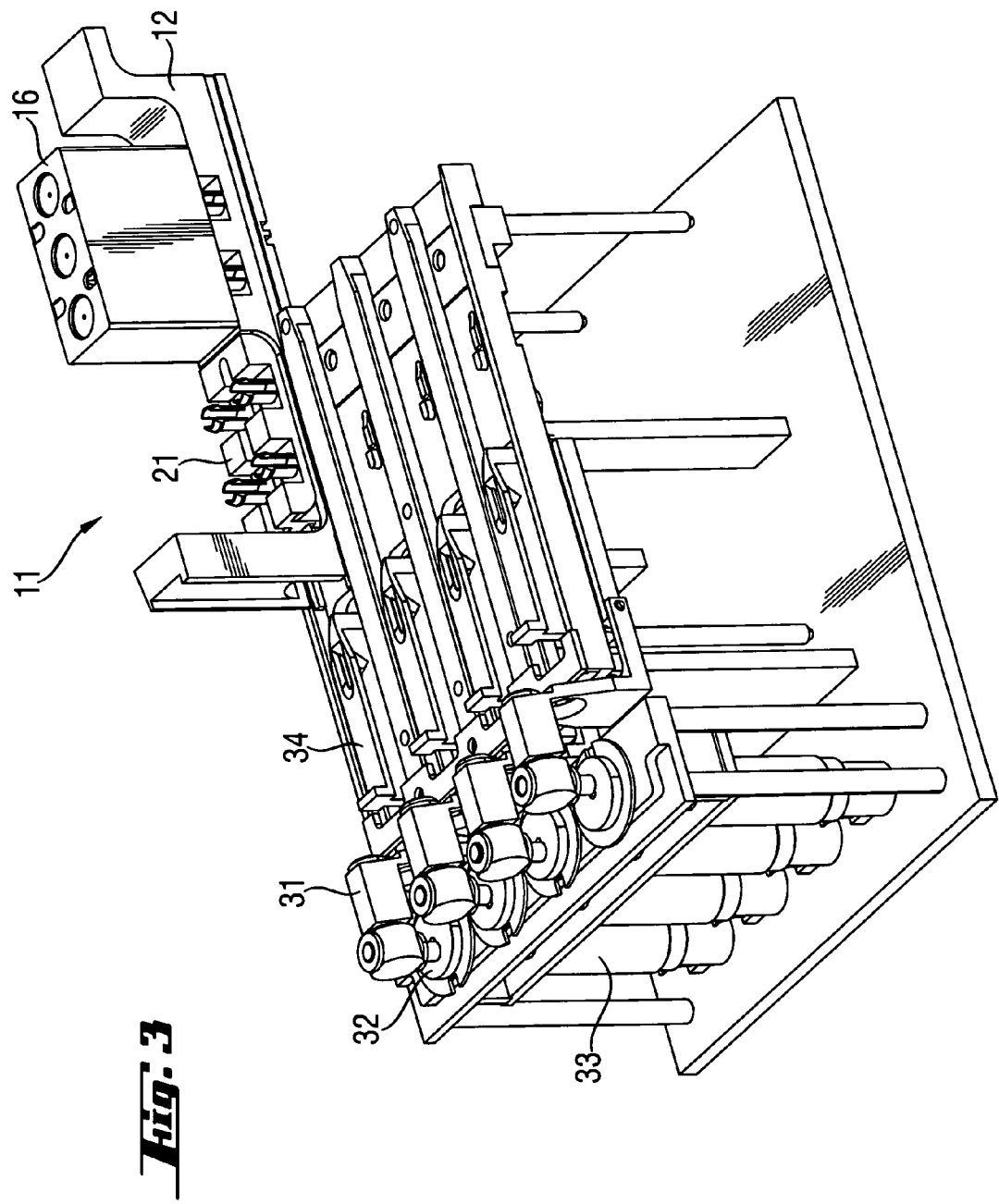
FIG. 3 shows a perspective view of a part of an analyzer according to the invention.

FIG. 3 shows a perspective view of a part of an analyzer according to the invention which includes a rack of the type described above with reference to FIGS. 1 and 2.

A first embodiment of a shaker device which is part of this analyzer is described hereinafter with reference to FIGS. 4 to 8.

As shown by FIG. 3, the analyzer may comprise several electromechanical shaker devices 31 each of which is adapted for being connected to a removable part 21 of rack 11.

Among the parts of shaker 31 represented in FIG. 3 are a carriage 34 and a disk 32 which carries an eccentric pin 36 and which is driven by a motor 33. In certain embodiments, motor 33 is a step motor.

Figure 4:
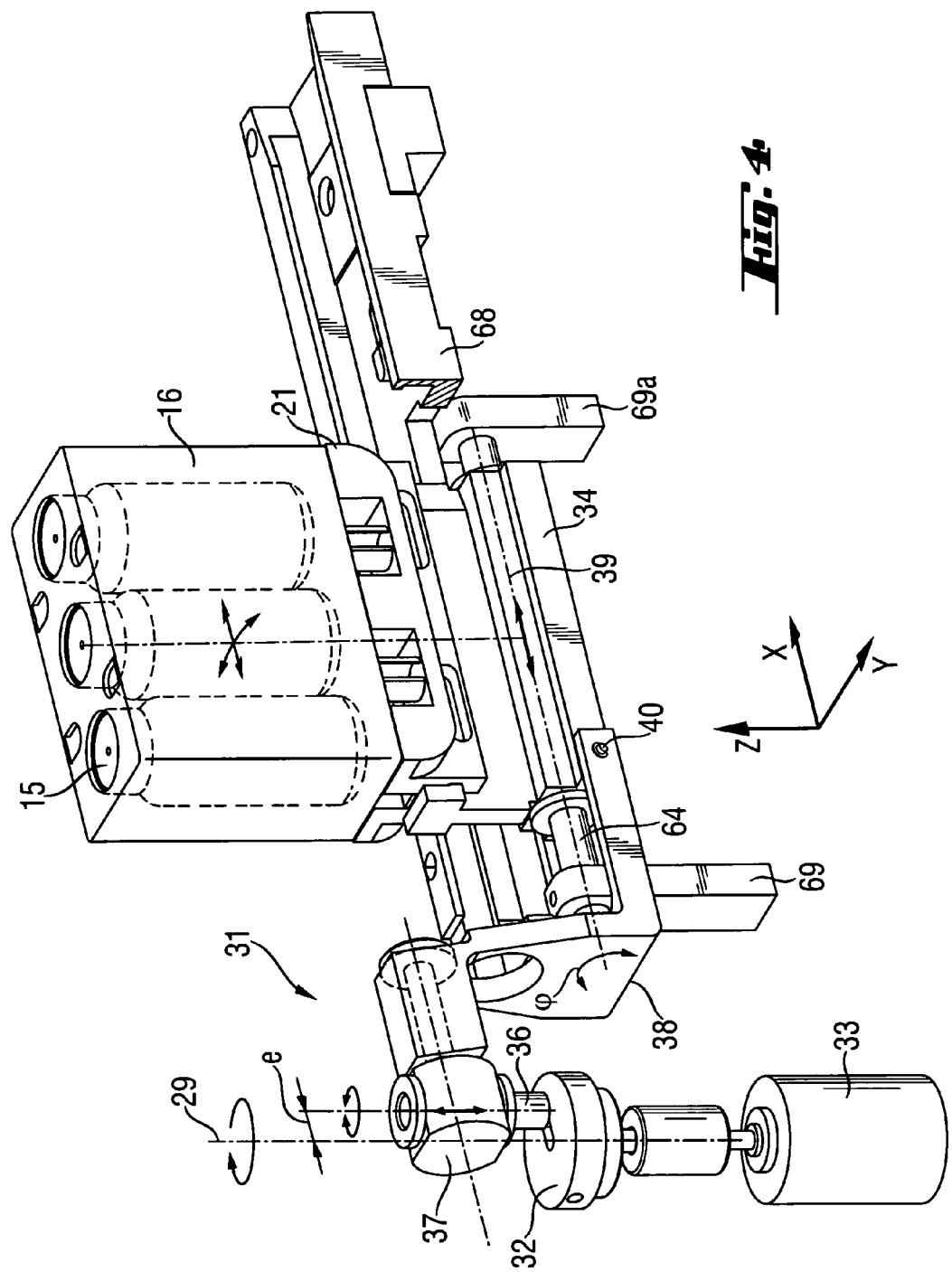
FIG. 4 shows a perspective view of a first embodiment of a shaker device 31 which is part of the analyzer of FIG. 3.

FIG. 4 shows a perspective view of shaker device 31. In FIG. 4 a carriage 34 which is part of shaker mechanism 31 is removably coupled to movable part 21 of rack 11. Carriage 34 is connected with a connection piece 38 by means of a joint 40. Connection piece 38 is rotatably connected to a cylindrical joint combined with a revolute joint 37 which is in turn connected with eccentric pin 36. The lower part of carriage 34 includes a slide bearing 53 which allows carriage 34 to slide back and forth along the length axis 39 of a guiding shaft 64 and also to oscillate back and forth around axis 39. Guiding shaft 64 has a fixed position and is parallel to the X-axis. Guiding shaft 64 is supported by support elements 69 and 69a respectively.

FIG. 4 also shows a support plate 68 for the frame 12 of rack 11.

As shown in FIG. 4, the eccentricity e is the distance that separates the axis of rotation 29 of motor 33 and the length axis of pin 36 from each other.

Figure 5:
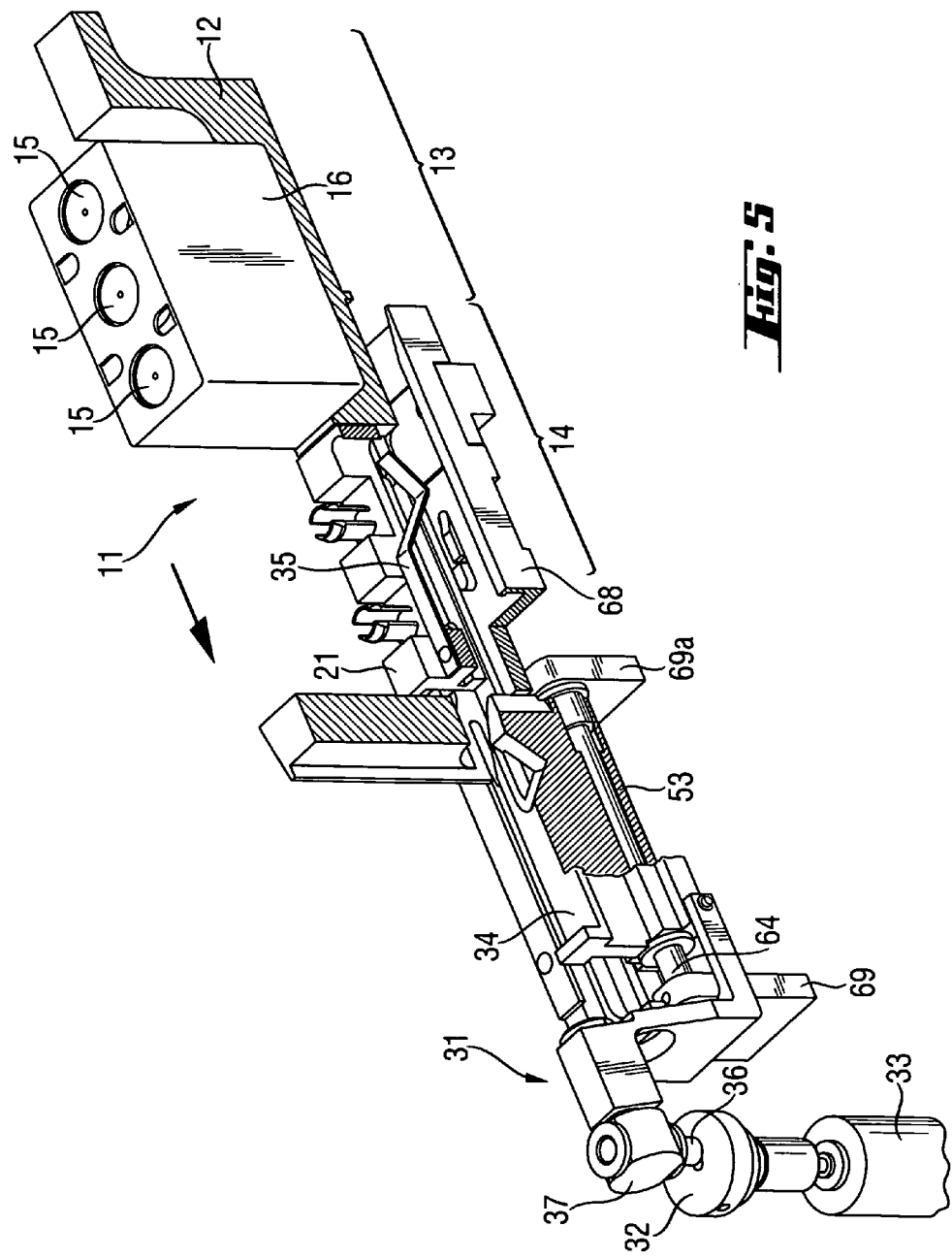
FIG. 5 shows a partial cross-sectional view of a means for removably coupling movable part 21 of rack 11 with a carriage 34 of a shaker device 31 by means of a leaf spring 35.
Figure 6:
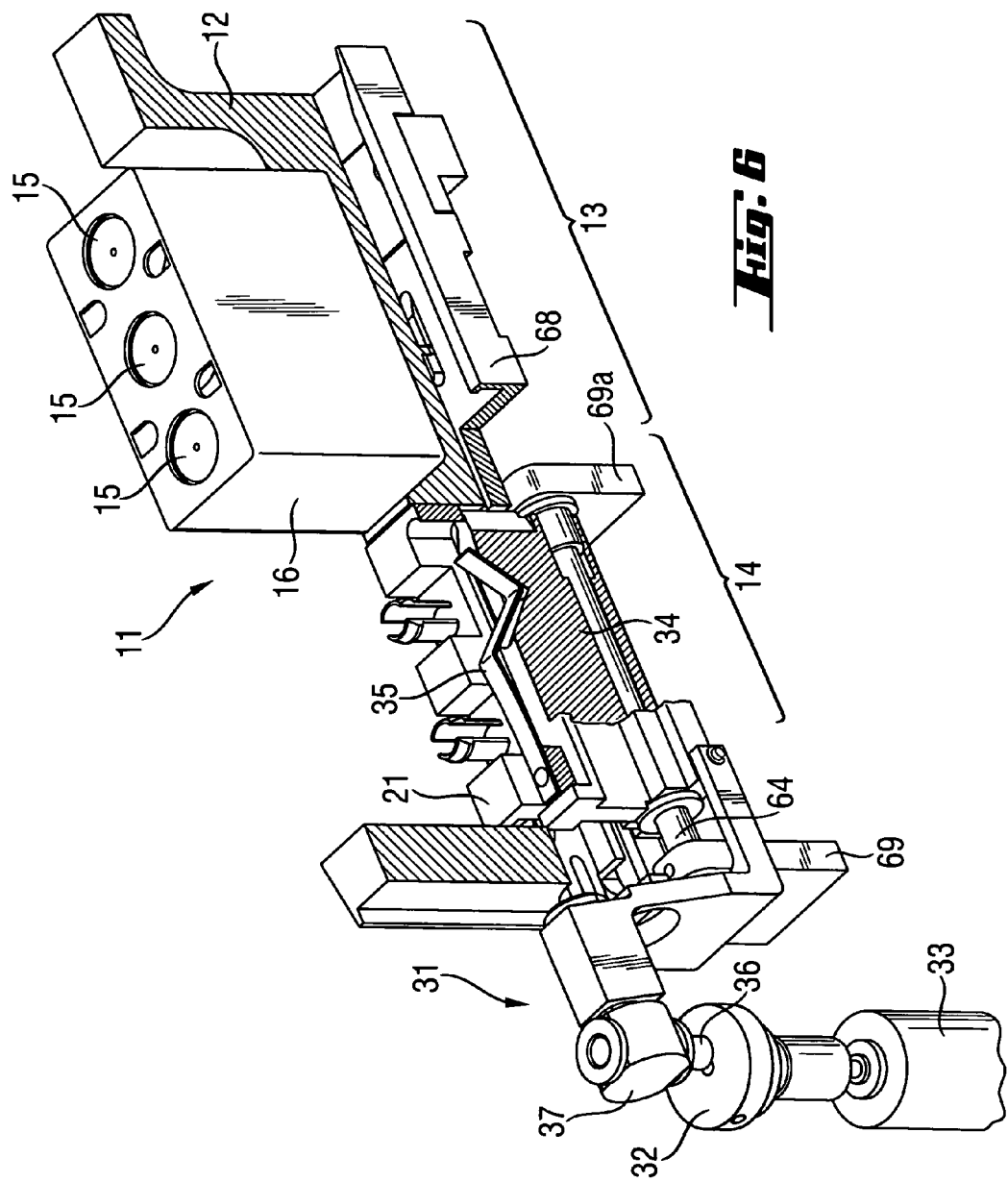
FIG. 6 shows a partial cross-sectional view of a movable part 21 of rack 11 coupled with carriage 34 of shaker device 31 by means of leaf spring 35.

FIG. 5 shows a partial cross-sectional view of means for removably coupling movable part 21 of rack 11 with a carriage 34 of a shaker device 31 by means of a leaf spring 35. As shown by FIGS. 5 and 6, one end of leaf spring 35 is mechanically connected with movable part 21. FIG. 5 shows a rack 11 in a position at which movable part 21 is not engaged with carriage 34 by means of a leaf spring 35. In FIG. 5, a casing 16 containing liquid containers 15 which do not have to be agitated is mounted on section 13 of rack 11. When frame 12 of rack 11 is in the position represented in FIG. 5 with respect to carriage 34 of shaker device 31, movable part 21 is loosely connected with frame 12. This loose connection may be achieved by means of pins 41, 42, 43 which cooperate with corresponding openings 51, 52 of removable part 21 shown in FIG. 2. Pins 41, 42, 43 are inserted in suitable openings of frame 12.

FIG. 6 shows a partial cross-sectional view of a movable part 21 of rack 11 coupled with carriage 34 of shaker device 31 by means of leaf spring 35. When frame 12 of rack 11 is in the position represented in FIG. 6 with respect to carriage 34 of shaker device 31, movable part 21 remains connected with frame 12.

As can be appreciated from FIG. 4, when disk 32 and thereby eccentric pin 36 are rotated by actuation of motor 33, pin 36 and joint 37 cause a movement of connection piece 38 and thereby of carriage 34, movable part 21 and liquid containers 15 in three orthogonal directions X, Y, Z within predetermined limits. Directions X, Y, Z are represented in FIG. 4. This motion is the result of the combination of two movements of connection piece 38: an oscillation of an angle φ around axis 39 and a back and forth motion in X direction.

The mechanical components of shaker device 31 may be made of any suitable material, such as, for example, aluminum or steel.

Figure 7:
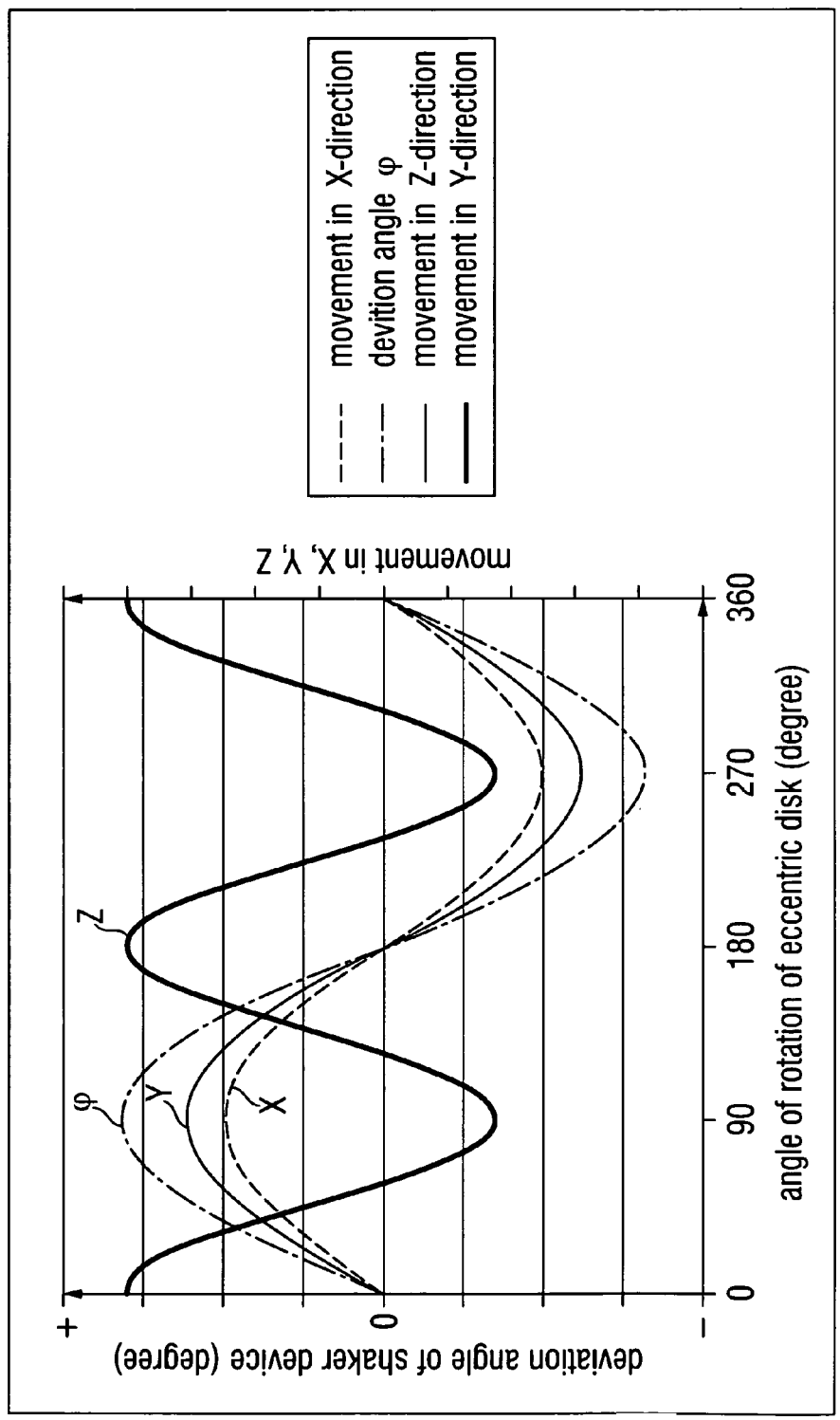
FIG. 7 shows curves representing the variation with time of the components of motion of carriage 34 in three orthogonal directions X, Y, Z and of an angular component φ corresponding to the oscillation of the carrier around an axis of oscillation.

FIG. 7 shows curves representing the variation with time of the components of motion of carriage 34 in three orthogonal directions X, Y, Z and of an angular component φ corresponding to the oscillation of carriage 34 around axis 39.

FIG. 8 shows a three-dimensional path M of motion of a point of casing 16 when it is moved by shaker device 31 shown by FIG. 4.

An encoder 28 (shown in FIG. 9) is connected with motor 33 and is arranged in the housing of motor 33. The angular position of motor 33 is controlled by means of the encoder 28 which for this purpose receives signals from an electro-optical position detector 66 described hereinafter with reference to FIGS. 9 and 10. Control of the angular position of motor 33 by means of encoder 28 and detector 66 makes it possible to position liquid container carrier 16 and thereby liquid container 16 in a reproducible way, at a predetermined position, e.g. at the end of a shaking operation of shaker device 31.

Example 3

Example of a Second Embodiment of an Analyzer According to the Invention

The structure of a second analyzer embodiment is similar to the structure of the first embodiment described above with reference to FIGS. 1-8, but this second analyzer embodiment comprises a second embodiment of a shaker device which is described hereinafter with reference to FIGS. 9 and 10.

Figure 9:
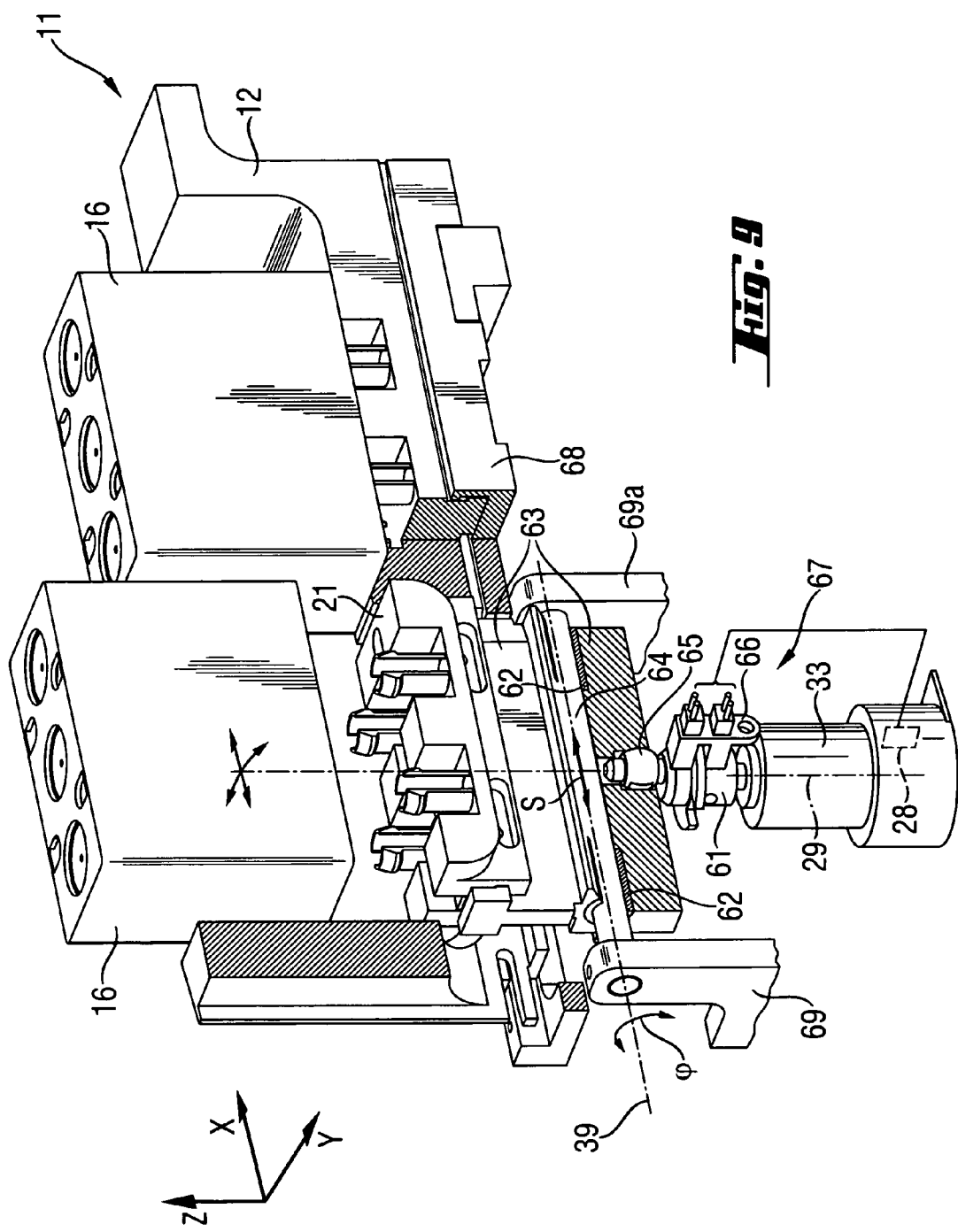
FIG. 9 shows a perspective partial view of a second embodiment of an analyzer according to the invention with a second embodiment of a shaker device.

FIG. 9 shows a perspective view of a shaker device 67 which is part of an analyzer according to the invention and which serves for moving the movable part 21 of rack 11 and thereby casing 16 in the same way as achieved with shaker 31 and thereby effect the motions represented in FIGS. 7 and 8.

Shaker device has a carriage 63 which has the same or similar structure and function as carriage 34 described above with reference to FIGS. 4-6. The lower part of carriage 63 includes a slide bearing 62 which allows carriage 34 to slide back and forth along the length axis 39 of a guiding shaft 64 and also to oscillate back and forth around axis 39. Guiding shaft 64 has a fixed position and is parallel to the X-axis. Guiding shaft 64 is supported by support elements 69 and 69a respectively.

Figure 10:
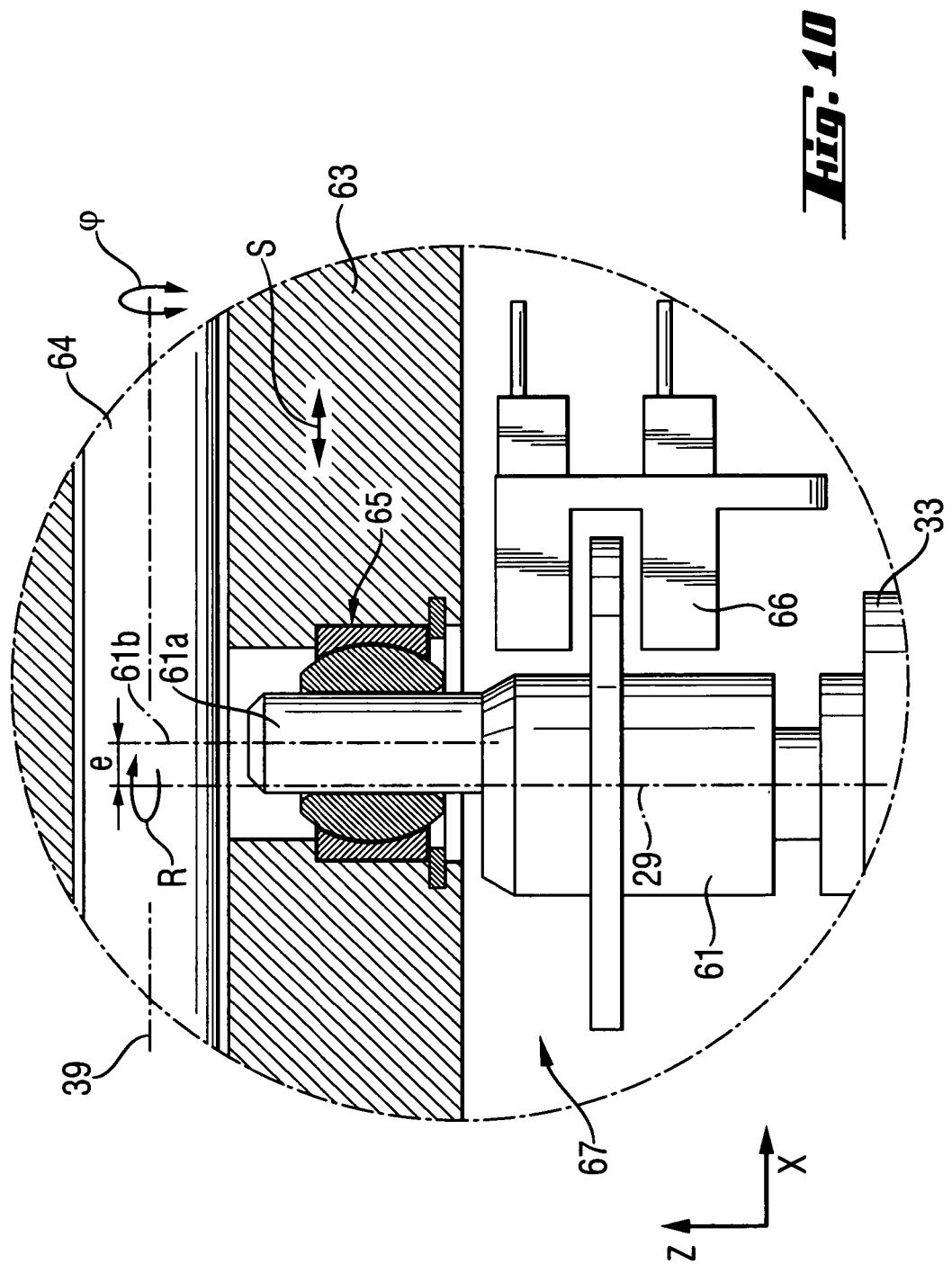
FIG. 10 shows an enlarged view of a portion of FIG. 9.

Shaker device 67 is shown in detail in FIG. 10. Shaker device 67 differs from shaker device 31 represented in FIG. 4 in that it comprises a pin 61a inserted in a ball and socket joint 65 which as shown in FIG. 9 is directly connected to carriage 63 of shaker device 67 and not by means of a joint 37 and a connection piece 38 as is the case when shaker device 31 shown in FIG. 4 is used. FIG. 9 also shows support plate 68 for the frame 12 of rack 11. Pin 61a is driven by a shaft 61 of a step motor 33.

FIG. 10 also shows the eccentricity e of pin 61a, i.e. the distance e between the length symmetry axis 61b of pin 61a and the rotation axis 29 of shaft 61 of motor 33.

The lower part of carriage 63 includes a slide bearing 62 which allows carriage 63 to slide back and forth along the length axis 39 of a guiding shaft 64 and also to oscillate back and forth around axis 39. Guiding shaft 64 has a fixed position and is parallel to the X-axis. Guiding shaft 64 is supported by support elements 69 and 69a respectively.

When motor 33 is actuated, a motion transmitted to carriage 63 by pin 61a and joint 65 moves carriage 63 back and forth along the length axis 39 of guiding shaft 64 and also oscillates carriage 63 back and forth around axis 39.

FIGS. 9 and 10 also show an electro-optical position detector 66 which accurately detects the angular position of motor shaft 61. Detector 66 provides signals to an encoder 28 (shown in FIG. 9) which serves for accurately positioning motor shaft 61. Control of the angular position of motor shaft 61 by means of encoder 28 and detector 66 makes it possible to position liquid container carrier 16 and thereby liquid container 16 in a reproducible way, at a predetermined position, e.g. at the end of a shaking operation of shaker device 67.

Example 4

Example of a Third Embodiment of an Analyzer According to the Invention

Figure 11:
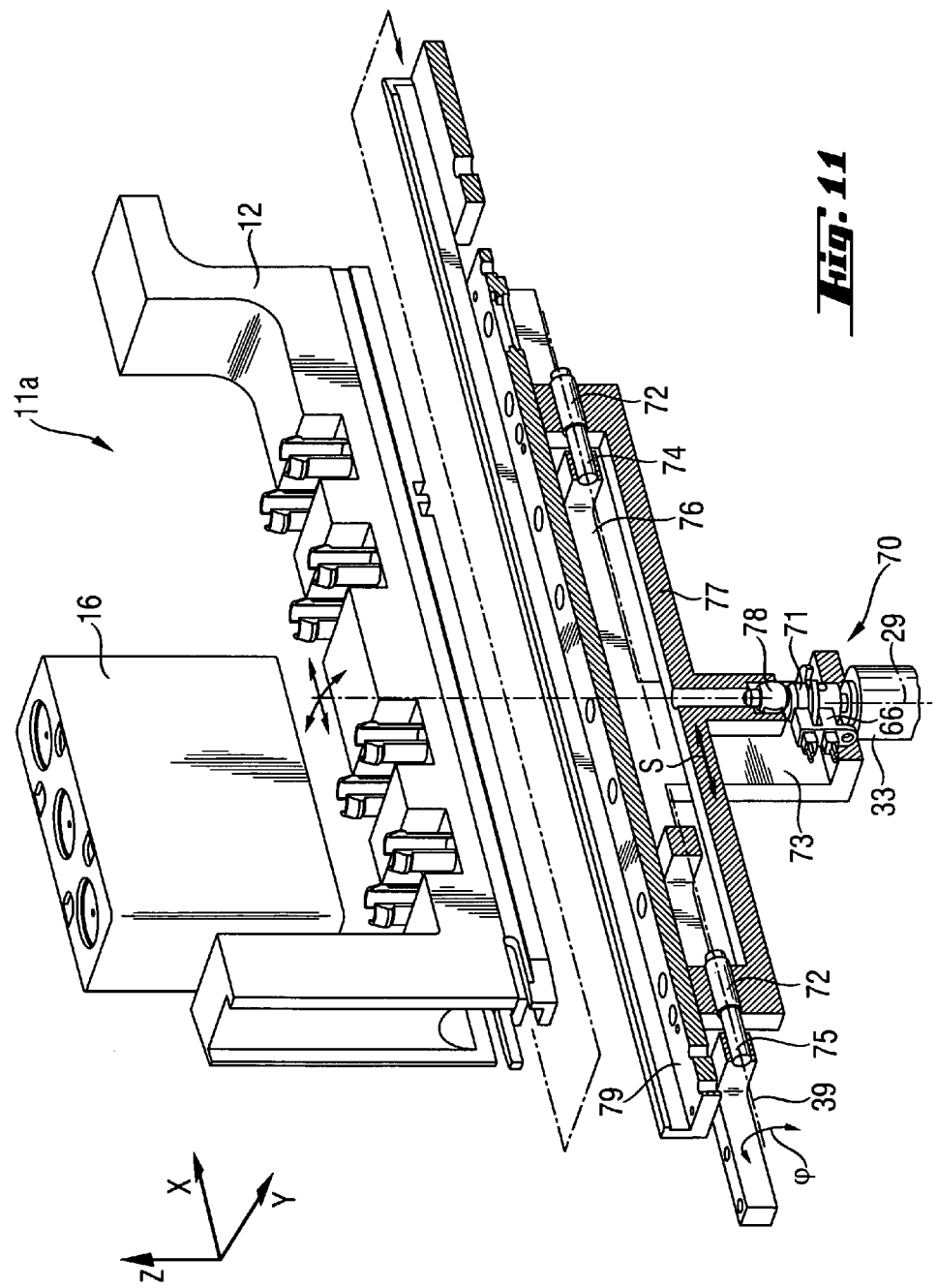
FIG. 11 shows a perspective partial view of a third embodiment of an analyzer according to the invention with a third embodiment of a shaker device.

FIG. 11 shows a part of a third embodiment of an analyzer according to the invention. This embodiment differs from the above described first and second embodiments in that it does not use the type of rack described above with reference to FIGS. 1 and 2, but a rack 11a built as a single piece frame 12 having a shape adapted for receiving liquid containers 16.

As shown by FIG. 11 the third embodiment of the analyzer also comprises a shaker device 70 which has a similar structure as shaker device 67 in FIG. 9. Shaker device 70 comprises a movable support plate 79 adapted for receiving rack 11a. Rack 11a and movable plate 79 are adapted for being removably connectable with each other.

The lower part of movable plate 79 is formed as a guiding support member 77.

Figure 12:
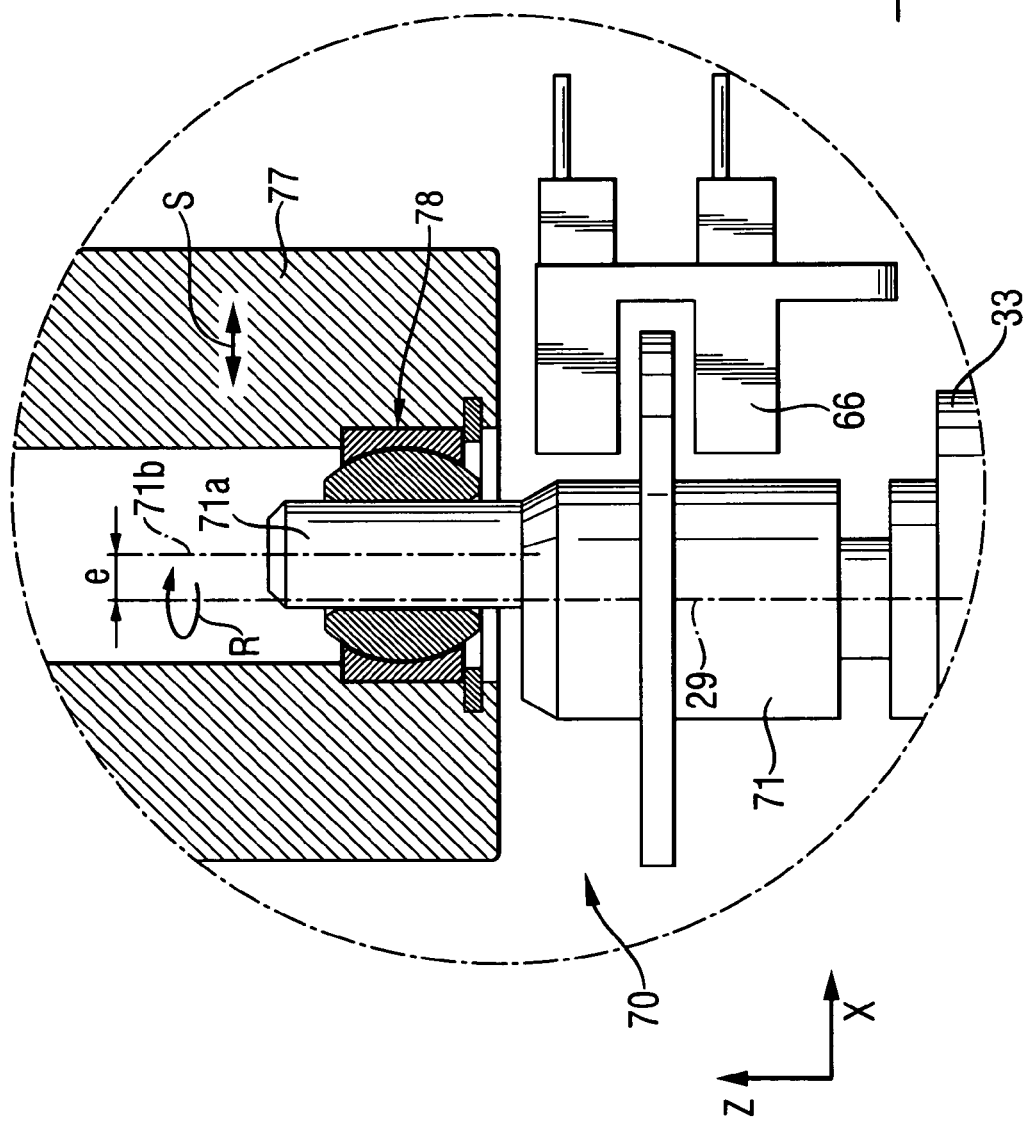
FIG. 12 shows an enlarged view of a portion of FIG. 11.

As shown by FIG. 12 shaker device 70 further comprises an eccentric pin 71a driven by a shaft 71 of a step motor 33.

Pin 71a is inserted in a ball and socket joint 78 which, as shown in FIG. 12, is directly connected to support member 77 of movable plate 79.

FIG. 12 also shows the eccentricity e of pin 71a, i.e. the distance e between the length symmetry axis 71b of pin 71a and the rotation axis 29 of shaft 71 of motor 33.

The lower part of guiding support member 77 includes a slide bearing 72 which allows support member 77 and thereby movable plate 79 to slide back and forth along the length axis 39 of a guiding shaft 75 and also to oscillate back and forth around axis 39. Guiding shaft 75 has a fixed position and is parallel to the X-axis.

When motor 33 is actuated, a motion transmitted to movable plate 79 by pin 71a and joint 78 moves movable plate 79 back and forth along the length axis 39 of guiding shaft 75 and also oscillates movable plate 79 back and forth around axis 39.

Shaker device 70 moves rack 11a and thereby casing 16 in the same way as achieved with shaker 31 in the embodiment described with reference to FIGS. 1-8. Casing 16 in FIG. 11 is thus moved by shaker device 70 as represented in FIGS. 7 and 8.

FIGS. 11 and 12 also show an electro-optical position detector 66 which accurately detects the angular position of motor shaft 71. Detector 66 provides signals to an encoder 28 (shown in FIG. 9) which serves for accurately positioning motor shaft 71. Control of the angular position of motor shaft 71 by means of encoder 28 and detector 66 makes it possible to position liquid container carrier 16 and thereby liquid container 16 in a reproducible way, at a predetermined position, e.g. at the end of a shaking operation of shaker device 70.

Example 5

Example of a Fourth Embodiment of an Analyzer According to the Invention

Figure 13:
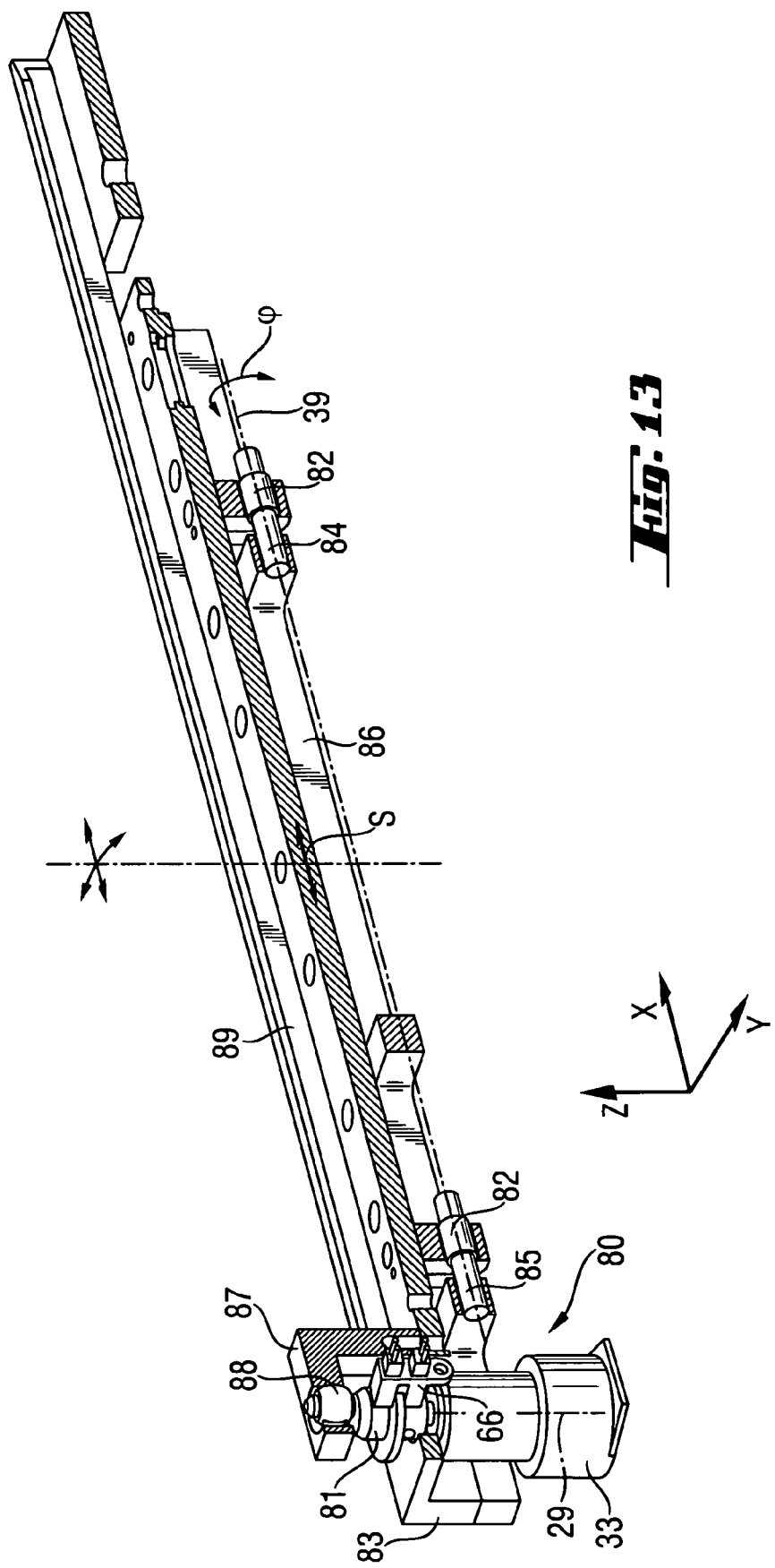
FIG. 13 shows a perspective partial view of a fourth embodiment of an analyzer according to the invention.

FIG. 13 shows a part of a fourth embodiment of an analyzer according to the invention. This fourth embodiment also uses a rack 11a of the type shown in FIG. 11 and comprises a movable support plate 89 similar to movable plate 79 of the third embodiment.

This fourth embodiment of an analyzer according to the invention differs from the above described third analyzer embodiment in that it comprises a shaker device 80 which is not connected to the lower and central part of the movable plate, but to one end thereof formed as a bar 87.

As shown by FIG. 13 shaker device 80 has a similar structure as shaker device 70 in FIG. 11.

Shaker device 80 comprises a movable support plate 89 adapted for receiving rack 11a. Rack 11a and movable plate 89 are adapted for being removably connectable with each other.

Figure 14:
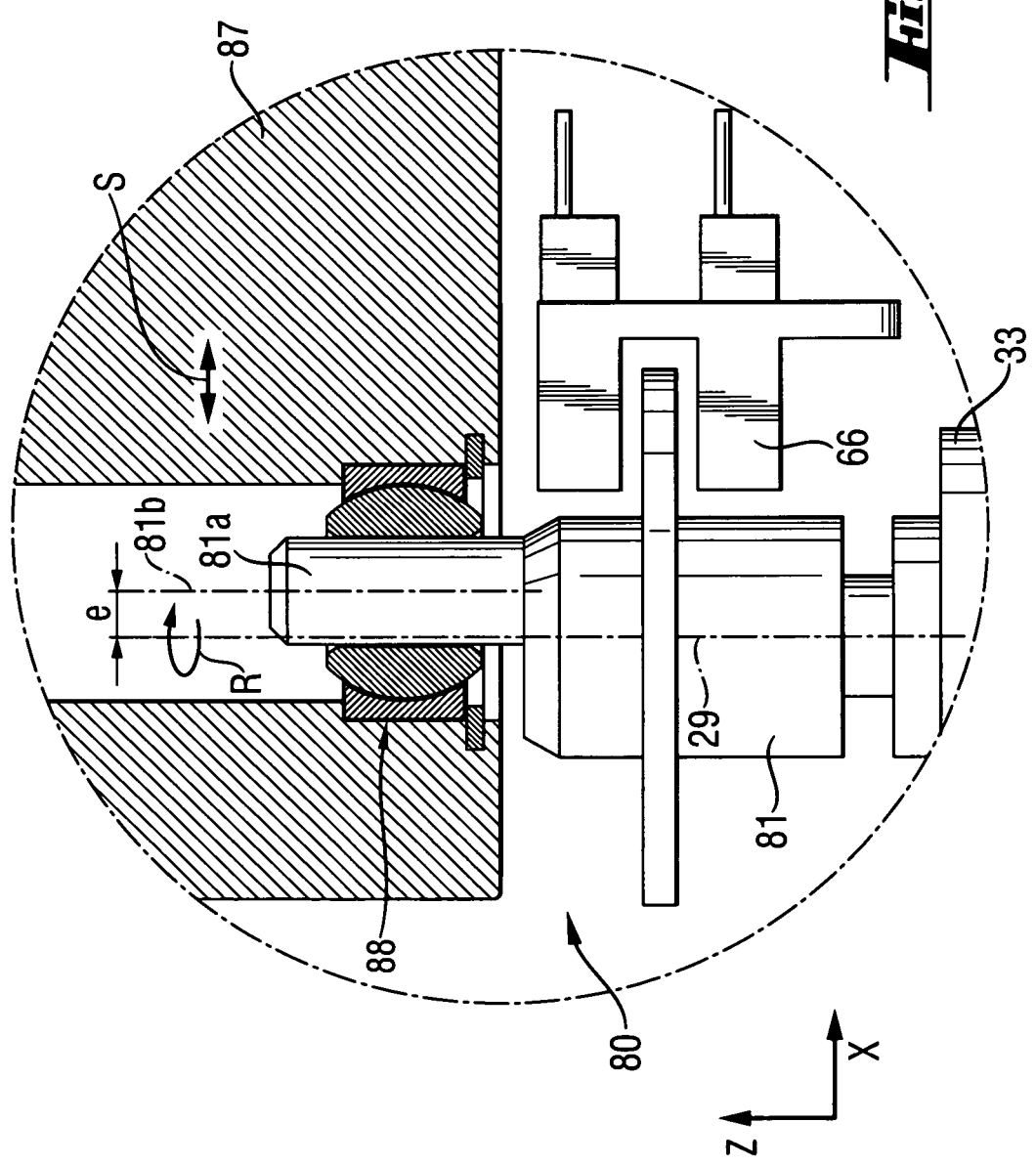
FIG. 14 shows an enlarged view of a portion of FIG. 13.

As shown by FIG. 14 shaker device 80 further comprises an eccentric pin 81a driven by a shaft 81 of a step motor 33.

Pin 81a is inserted in a ball and socket joint 88 which as shown in FIG. 14 is directly connected to bar 87 at one end of movable plate 89.

FIG. 14 also shows the eccentricity e of pin 81a, i.e. the distance e between the length symmetry axis 81b of pin 81a and the rotation axis 29 of shaft 81 of motor 33.

The lower part of movable plate 89 is formed as a guiding support member which includes slide bearings 82 which allow movable plate 89 to slide back and forth along the length axis 39 of guiding shafts 84 and 85 and also to oscillate back and forth around axis 39. Guiding shafts 84 and 85 have a fixed position and are parallel to the X-axis.

When motor 33 is actuated, motion transmitted to movable plate 89 by pin 81a and joint 88 moves movable plate 89 back and forth along the length axis 39 of guiding shafts 84 and 85 and also oscillates movable plate 89 back and forth around axis 39.

Shaker device 80 also moves rack 11a and thereby casing 16 in the same way as achieved with shaker 31 in the embodiment described with reference to FIGS. 1-8. Casing 16 in FIG. 11 is thus moved by shaker device 80 as represented in FIGS. 7 and 8.

FIGS. 13 and 14 also show an electro-optical position detector 66 which accurately detects the angular position of motor shaft 81. Detector 66 provides signals to an encoder 28 (shown in FIG. 9) which serves for accurately positioning motor shaft 81. Control of the angular position of motor shaft 81 by means of encoder 28 and detector 66 makes it possible to position liquid container carrier 16 and thereby liquid container 16 in a reproducible way, at a predetermined position, e.g. at the end of a shaking operation of shaker device 80.

Example 6

Example of a Fifth Embodiment of an Analyzer According to the Invention

The structure of a fifth analyzer embodiment is similar to the structure of the first embodiment described above with reference to FIGS. 1-8, but this second analyzer embodiment comprises a second embodiment of a shaker device which is described hereinafter with reference to FIGS. 15 to 17.

Figure 15:
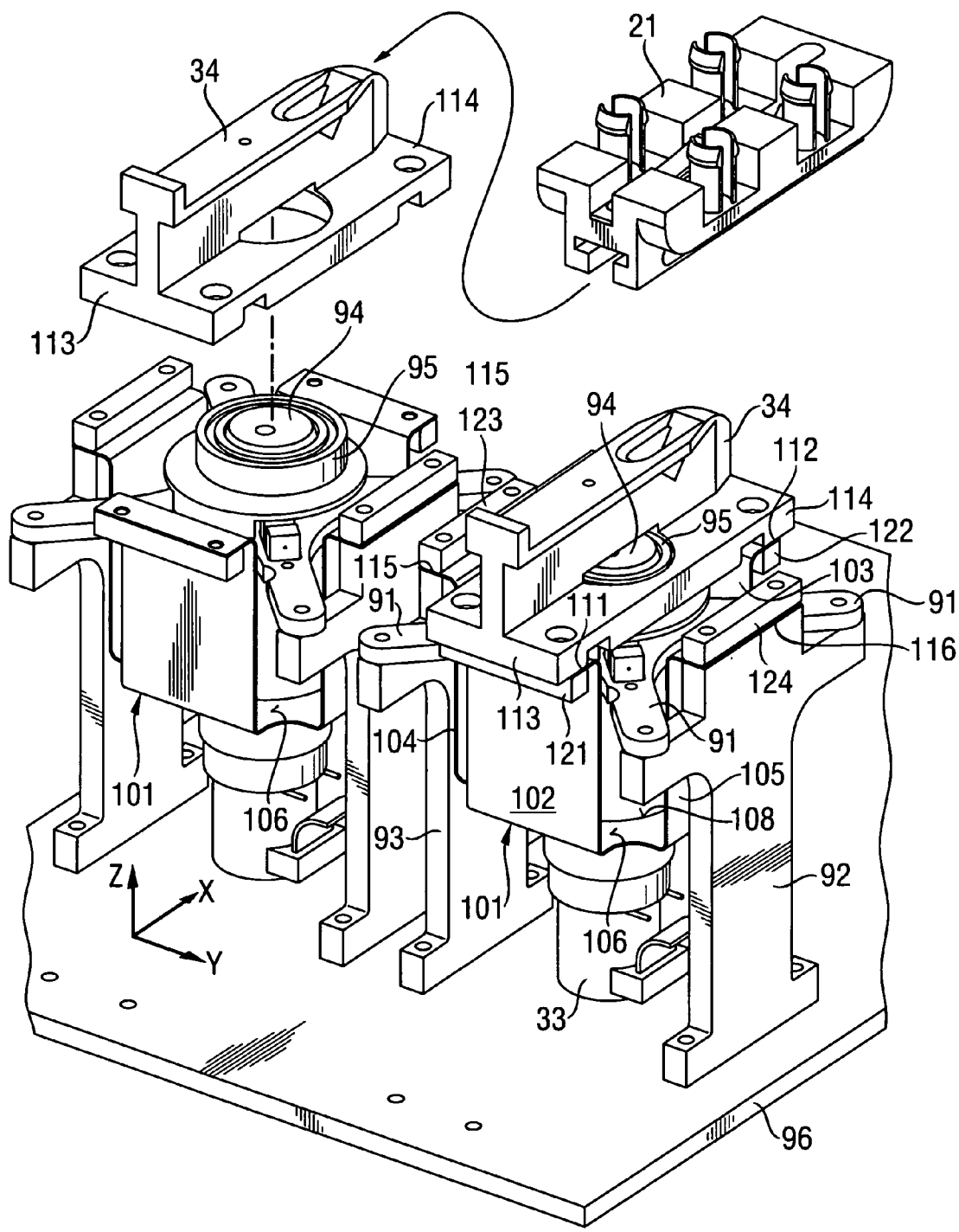
FIG. 15 shows a perspective partial view of a fifth embodiment of an analyzer according to the invention with a fourth embodiment of a shaker device.

FIG. 15 shows a perspective view of two separate shaker devices side by side. Each shaker device is mounted on a basis plate 96 of the analyzer and comprises a movable carriage 34 adapted for being removably connected to the movable part 21 of a rack 11 as described above with reference to FIGS. 1-6, rigid support plates 92 and 93 fixedly mounted on basis plate 96, and a cross-shaped support plate 91, on which is mounted the motor 33 of the shaker device. Support plates 92 and 93 are arranged on opposite sides of movable carriage 34.

As shown by FIG. 15, movable carriage 34 is connected to support plates 92, 93 by means of a flexible element 101.

The connection of movable carriage 34 to stationary rigid support plates 92, 93 by means of flexible element 101 allows limited displacements of movable carriage 34 in three directions X, Y, Z which are orthogonal to each other. The material and the dimensions of the central part 106 and the flaps 102-105 of flexible element 101 are so chosen that this element has sufficient flexibility to allow such displacements. In one particular embodiment, flexible element 101 is made of stainless spring band steel No. 1.4310 and has the following dimensions: Width=35 mm, Length=50 mm and Thickness=0.2 mm.

Figure 16:
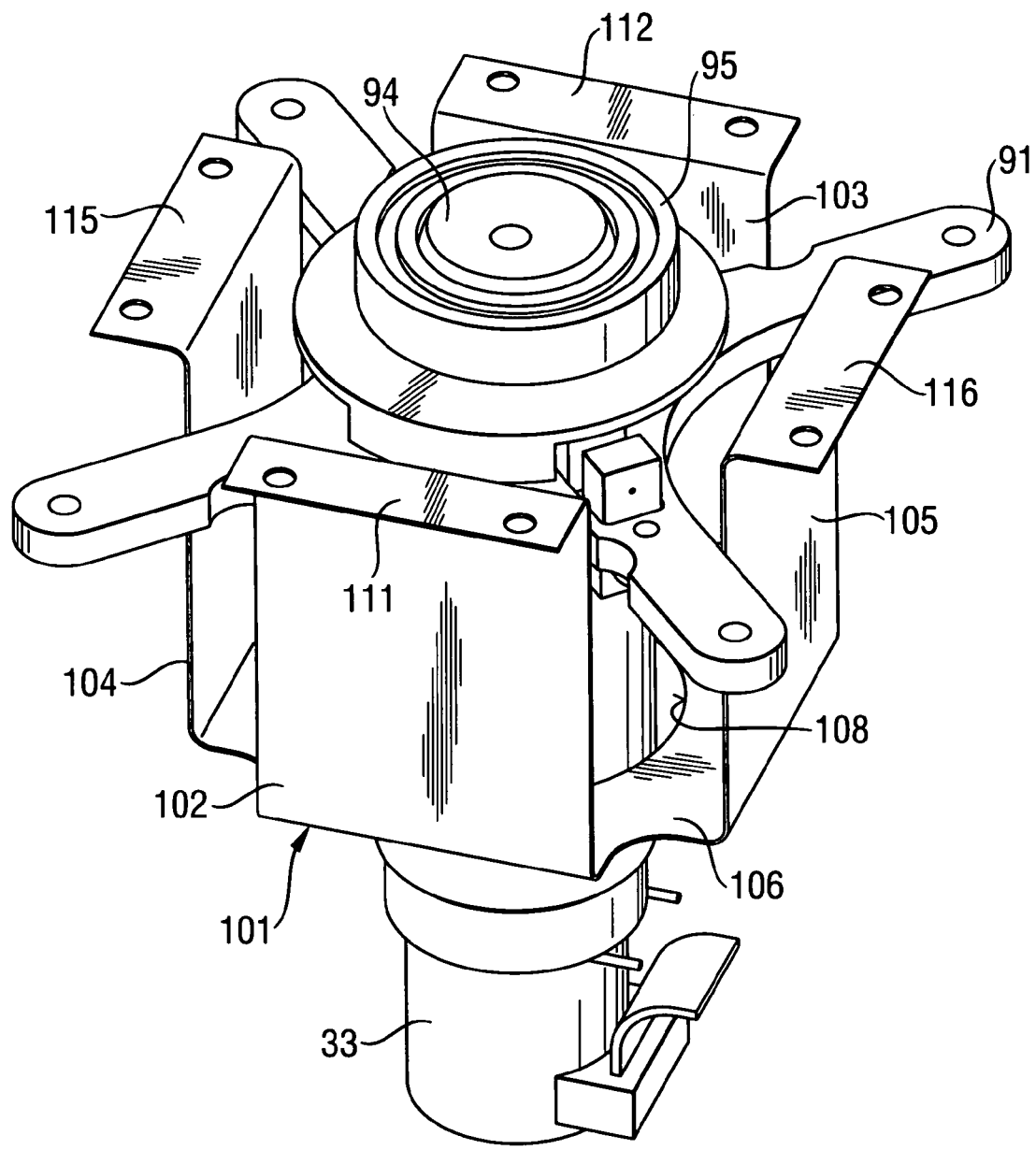
FIG. 16 is a perspective view of a part of the shaker embodiment shown by FIG. 15.
Figure 17:
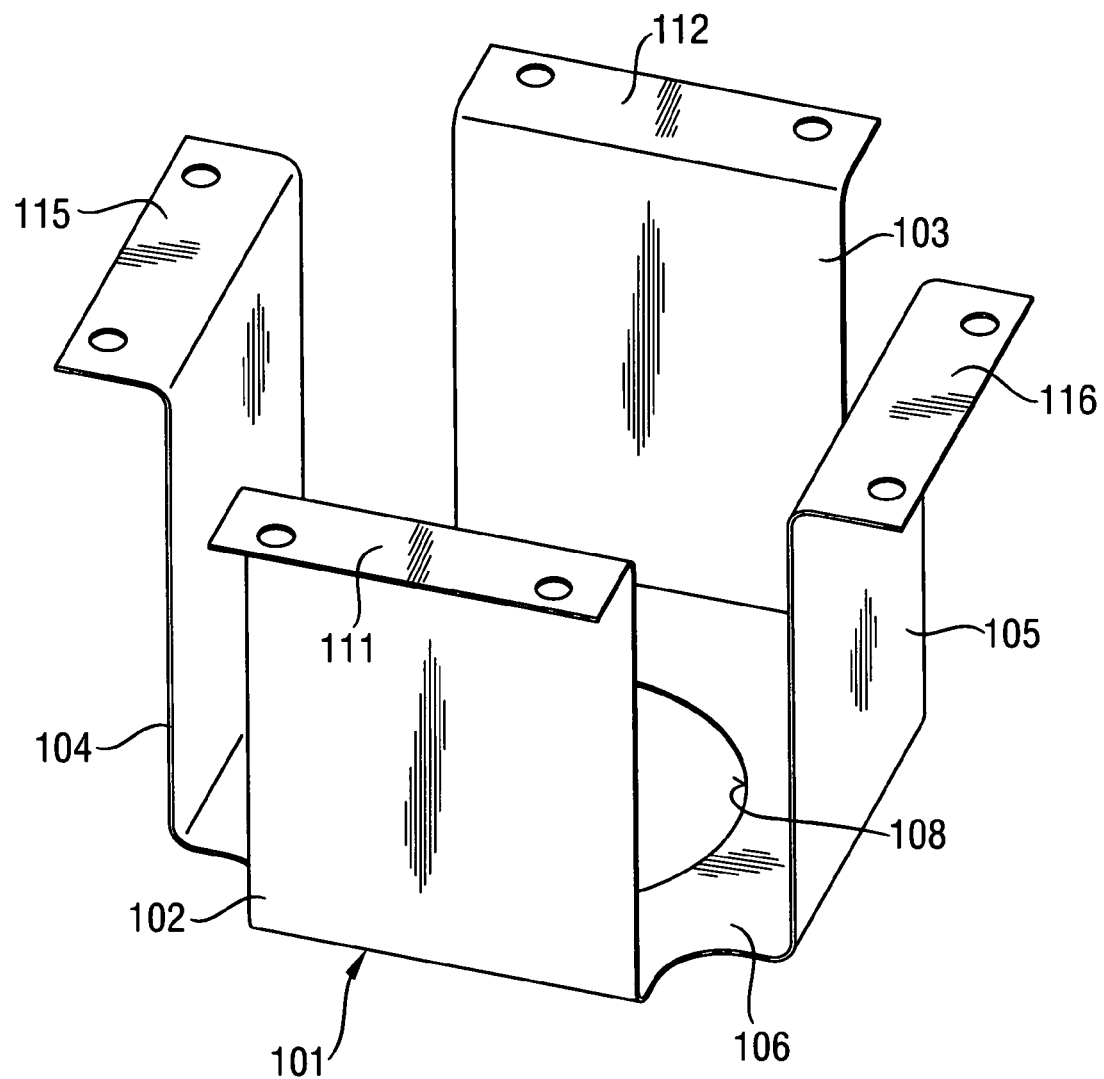
FIG. 17 is a perspective view of the flexible element 101 shown in FIG. 15.

In one embodiment flexible element 101 is a single-piece element which, as shown by FIGS. 16 and 17, comprises a flat central part 106 which lies in a plane, a first pair of rectangular flaps 102, 103 parallel to each other, and a second pair of rectangular flaps 104, 105 parallel to each other. Flaps 104 and 105 extend along planes which are normal to flaps 102, 103.

As shown in FIG. 15, the shaft of motor 33 passes through an opening 108 of flexible element 101 and drives an eccentric ball 94 which cooperates with a roller bearing 95 and moves carriage 34.

Each of flaps 102, 103 extends from central part 106 along a plane normal to the plane defined by the surface of central part 106. Flaps 102 and 103 have end parts 111 and 112 respectively. End parts 111, 112 are connected to end parts 113 respectively 114 of said movable carriage 34. End parts 113 and 114 lie on opposite sides of movable carriage 34.

Each of flaps 104, 105 extend from central part 106 along a plane normal to the plane defined by the surface of central part 106. Flaps 104, 105 have end parts 115 and 116 respectively. End part 115 is connected to stationary support plate 93. End part 116 is connected to stationary support plate 92.

The embodiment just described offers the advantage of having less number of parts than the other shaker embodiments described above, and this reduces the manufacturing costs and makes the operation more reliable and less prone to failure due to mechanical problems.

Figure 18:
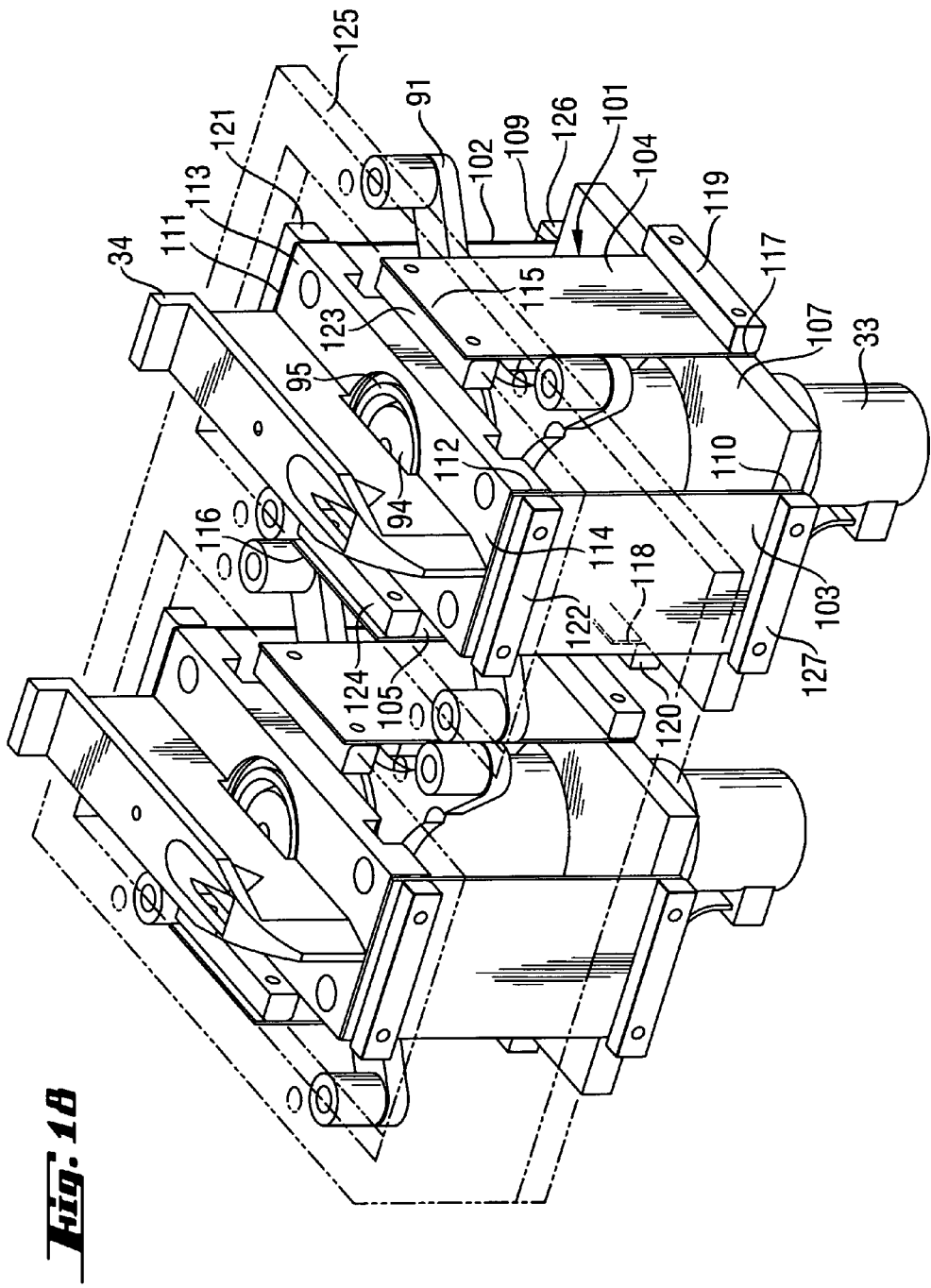
FIG. 18 shows a perspective partial view of a variant of the embodiment of a shaker device of FIG. 15.
Figure 19:
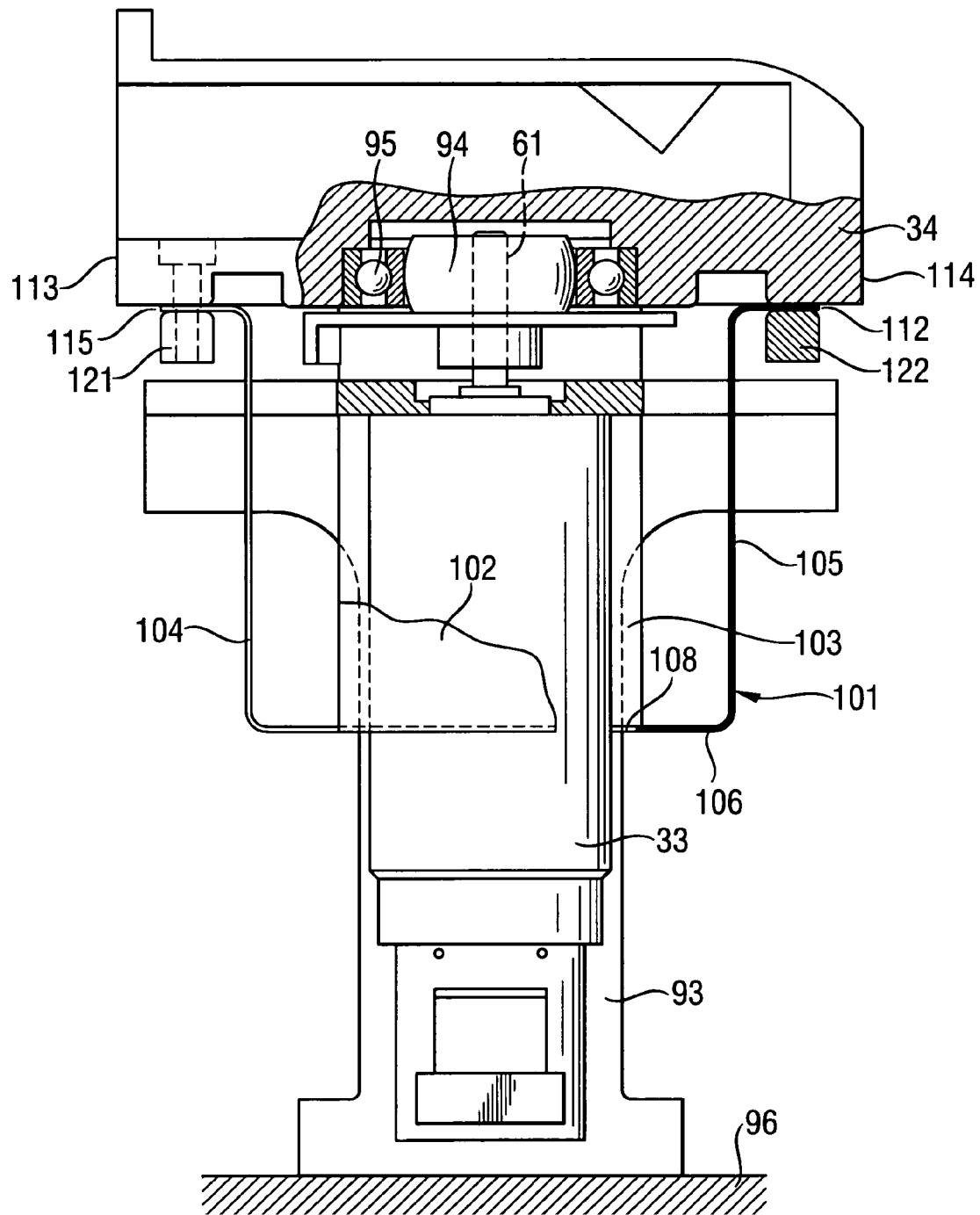
FIG. 19 shows a partial view of the connection between carriage 34 and motor 33.

In another embodiment represented in FIG. 18, the shaker device is mounted on an intermediate support plate 125 of the analyzer instead of support plates 92 and 93, and flexible element 101 is not a single-piece element, but is a structure which comprises a central plate 107 lying in a plane, a first pair of individual rectangular flaps 102, 103 parallel to each other and a second pair of individual rectangular flaps 104, 105 parallel to each other. Flaps 104 and 105 extend along planes which are normal to flaps 102 and 103.

Each of flaps 102, 103 has a first end part 109, 110 connected to central plate 107 by connecting pieces 126, 127 and a second end part 111 respectively 112 which are connected to end parts 113 and 114 of movable carriage 34 by means of connecting pieces 121 respectively 122. End parts 113 and 114 lie on opposite sides of movable carriage 34. The first end parts of flaps 102 and 103 may be connected to plate 107 by connecting pieces similar to connecting pieces 121, 122.

Flap 104 has a first end part 117 connected by connecting piece 119 to central plate 107 and a second end part 115 opposite to the first end part and connected by a connecting piece 123 to intermediate support plate 125 of the analyzer at a place located on one side of said movable carriage 34, whereas flap 105 has a first end part 118 connected by a connecting piece 120 to central plate 107 and a second end part 116 opposite to the first end part and connected by connecting piece 124 to intermediate support plate 125 of the analyzer at a place located on the opposite side of movable carriage 34.

Figure 20:
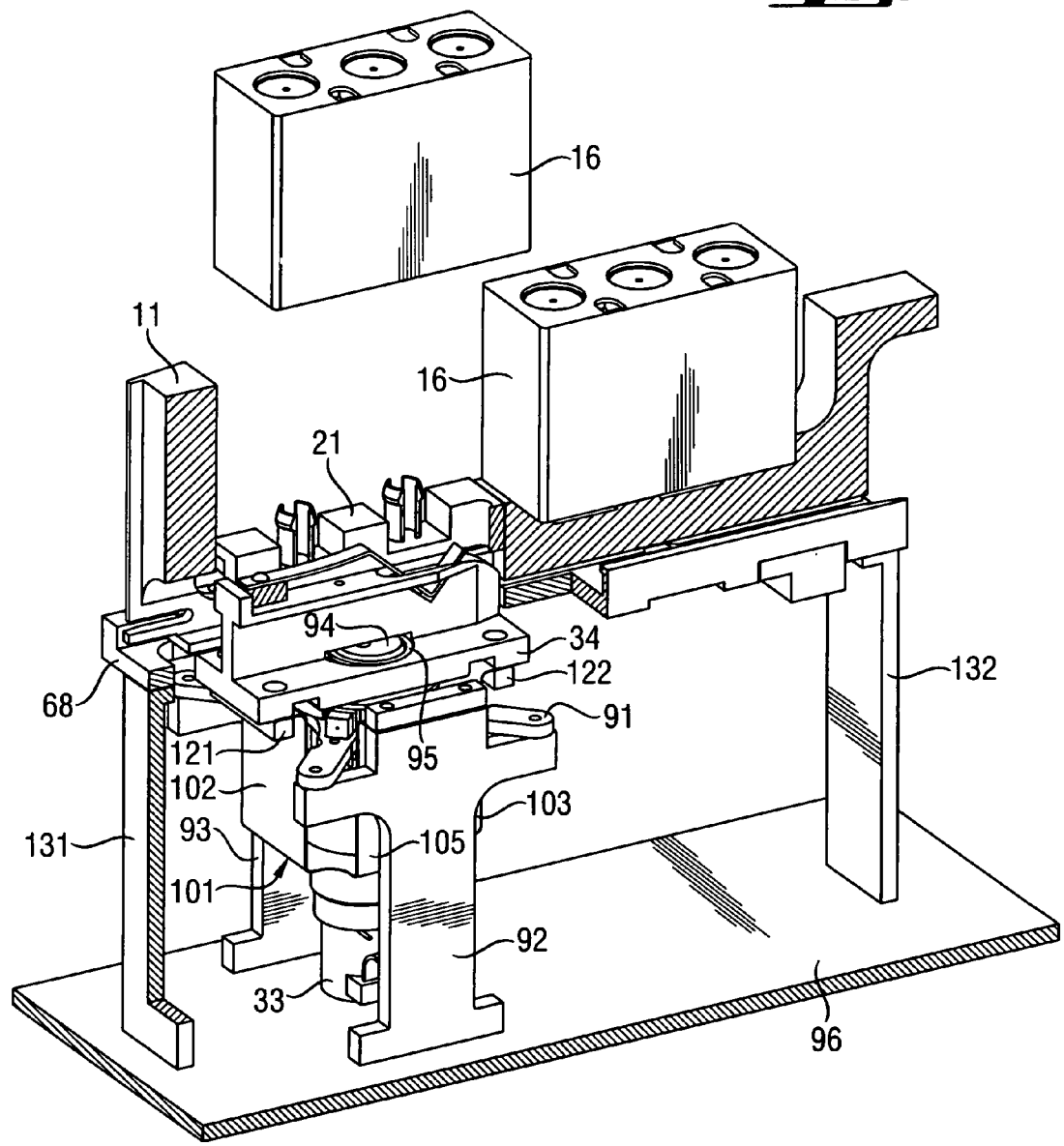
FIG. 20 illustrates the use of a shaker device of FIG. 15 in an analyzer of the type described with reference to FIGS. 1-8.

FIG. 20 illustrates the use of a shaker device of the type described above with reference to FIGS. 15-17 in an analyzer in which a casing 16 containing one or more reagent containers is positioned on the movable part 21 of a rack and this movable part is removably connected to the movable carriage 34 of the shaker device. FIG. 20 includes a partial view of a rack 11 of the type shown in FIGS. 1-6, a part of a support plate 68 and a part of support elements 131 and 132 which support plate 68. Support elements 131 and 132 are rigidly connected with basis plate 96.

Figure 21:
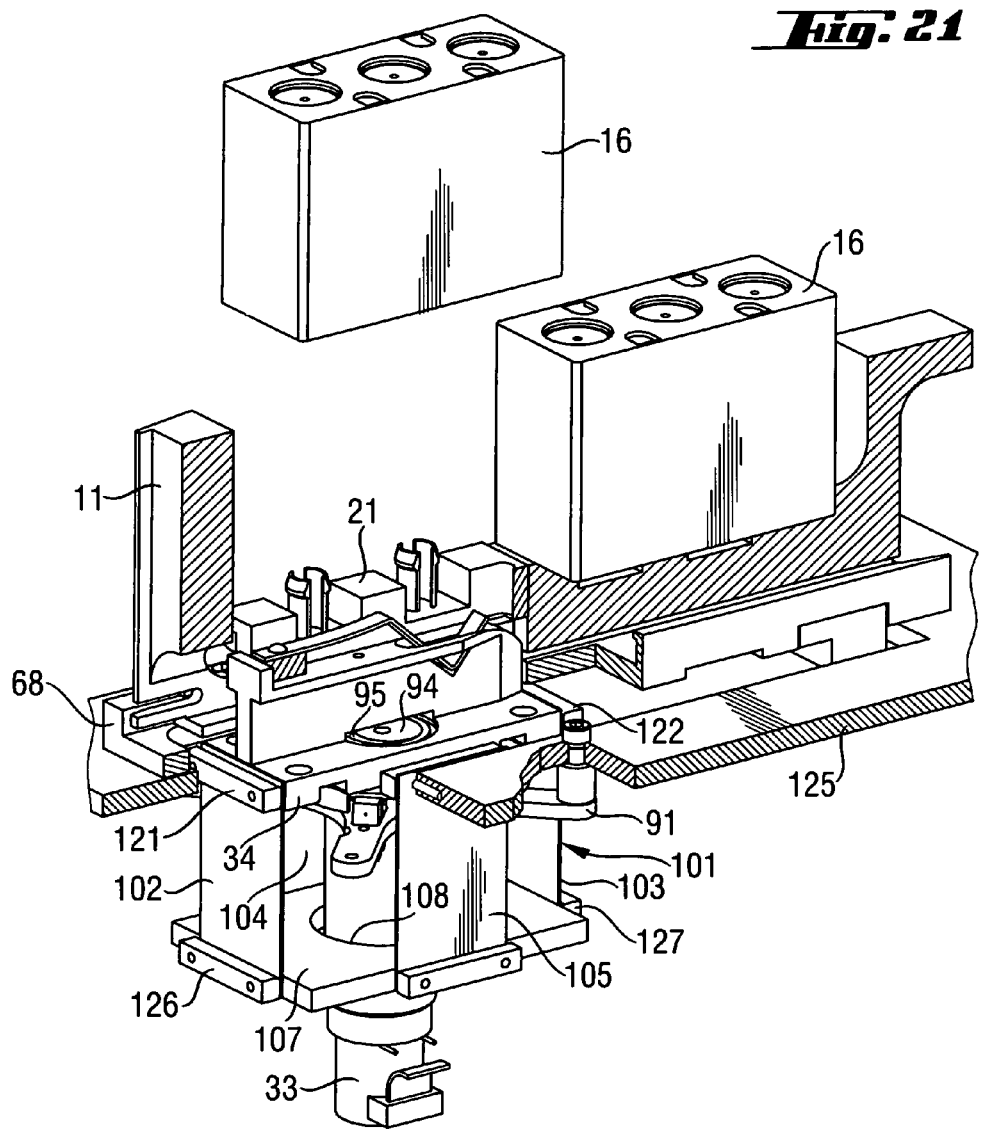
FIG. 21 shows a variant of the embodiment of FIG. 20.

FIG. 21 shows a partial perspective view of a variant of the embodiment shown by FIG. 20, wherein instead of a single-piece flexible element 101 a flexible structure of the type described above with reference to FIG. 18 is used.

Figure 22:
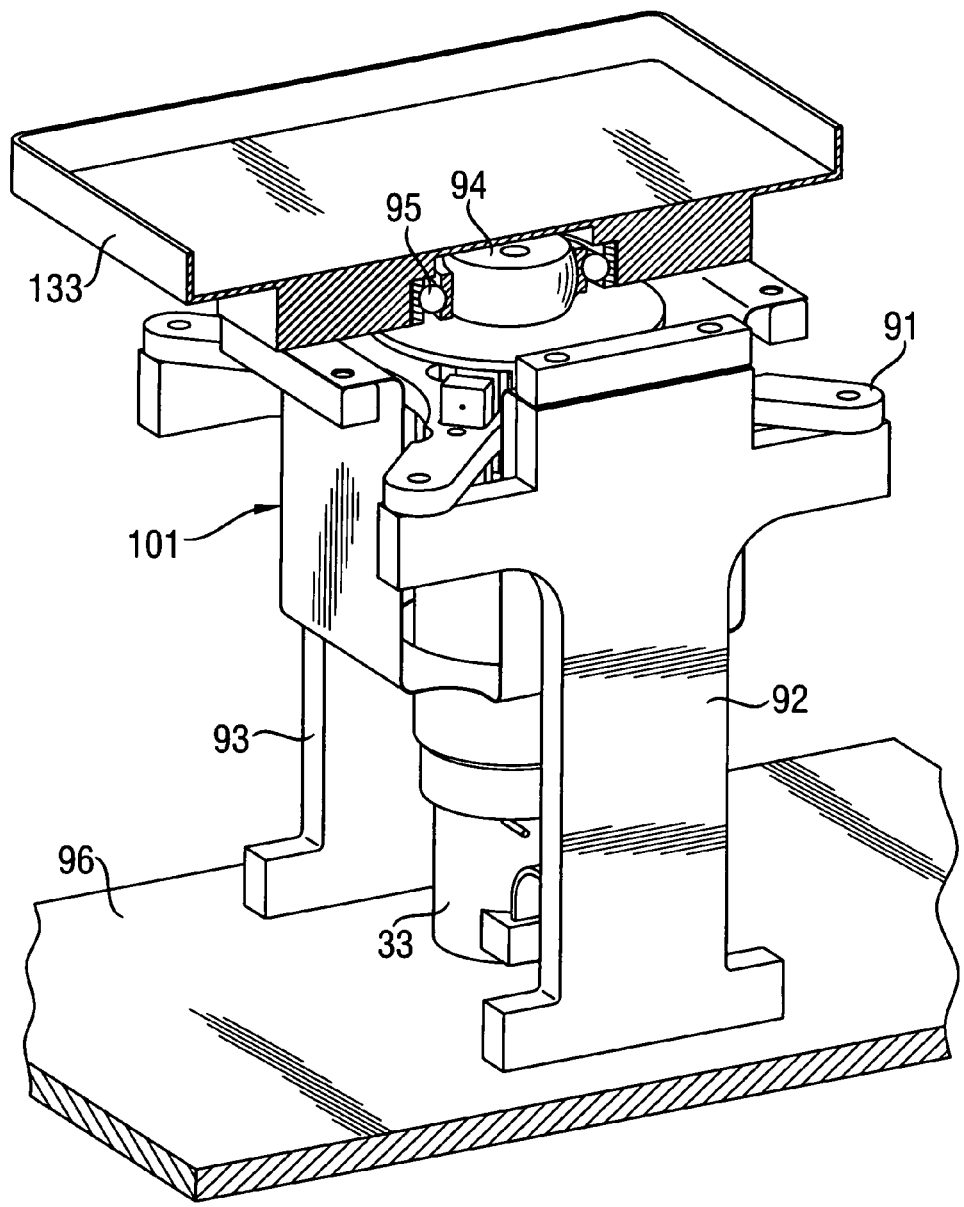
FIG. 22 illustrates the use of a shaker device of the type shown by FIG. 15 in an analyzer of FIG. 11.

FIG. 22 illustrates the use of a shaker device of the type described above with reference to FIGS. 15-17 in an analyzer in which a tray 133 is used as carrier of liquid containers that have to be agitated during some time intervals. FIG. 23 shows a variant of the embodiment shown by FIG. 22, wherein instead of a single-piece flexible element 101a flexible structure of the type described above with reference to FIG. 18 is used.

Although preferred embodiments of the invention have been described using specific terms, such description is for illustrative purposes only, and it is to be understood that changes and variations may be made without departing from the spirit or scope of the following claims.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A rack for holding containers containing liquids, said rack comprising:

(a) a frame having sections, each section being adapted for receiving a liquid containing component;

(b) a first section of said frame being adapted for receiving a first liquid containing component adapted for being removably but tightly mechanically connected to said first section;

(c) a second section of said frame comprising a recessed housing chamber with a defined length flanked by opposing side walls, wherein a movable part sits in said recessed housing chamber, said movable part having a length that is shorter than the length of the recessed housing chamber, wherein said side walls define permitted limits of movement for said movable part sitting in said recessed housing chamber, said movable part containing means for coupling to a shaker device, said movable part further containing one or more means for receiving and holding a second liquid containing component, said movable part being loosely connected to said second section of the frame by means of pins cooperating with openings in said second section of the frame and corresponding openings in said movable part; and wherein said movable part transmits motion to said second liquid containing component within the second section, while no motion is transmitted to said first liquid containing component within the first section.

2. The rack according to claim 1, wherein said movable part remains connected with said frame when said movable part is coupled to said shaker device.

3. The rack according to claim 1, wherein said at least one movable part and said second liquid containing component are movable within predetermined limits in three directions (X, Y, Z) which are orthogonal to each other.

4. The rack of claim 1, wherein said means for coupling said movable part to a shaker device comprise a leaf spring.

* * * * *